US011617856B2

(12) United States Patent
Goral et al.

(10) Patent No.: US 11,617,856 B2
(45) Date of Patent: *Apr. 4, 2023

(54) CATHETER ASSEMBLY WITH SEAL MEMBER

(71) Applicant: SMITHS MEDICAL ASD, INC., Plymouth, MN (US)

(72) Inventors: David J. Goral, Brookfield, CT (US); Christopher D. Roehl, New Hartford, CT (US); James M. Muskatello, Southington, CT (US); Mahesh Munavalli, Middleton, MA (US); Jocelyn C. Michaud, Bristol, CT (US)

(73) Assignee: Smiths Medical ASD, Inc., Plymouth, MN (US)

( * ) Notice: Subject to any disclaimer, the term of this patent is extended or adjusted under 35 U.S.C. 154(b) by 740 days.

This patent is subject to a terminal disclaimer.

(21) Appl. No.: 16/110,111

(22) Filed: Aug. 23, 2018

(65) Prior Publication Data
US 2018/0361120 A1    Dec. 20, 2018

Related U.S. Application Data

(60) Continuation of application No. 15/190,017, filed on Jun. 22, 2016, now Pat. No. 10,080,867, which is a
(Continued)

(51) Int. Cl.
*A61M 25/00* (2006.01)
*A61M 25/06* (2006.01)
*A61M 25/01* (2006.01)

(52) U.S. Cl.
CPC .... *A61M 25/0097* (2013.01); *A61M 25/0009* (2013.01); *A61M 25/0014* (2013.01);
(Continued)

(58) Field of Classification Search
CPC .......... A61M 25/0097; A61M 25/0014; A61M 25/0618; A61M 25/0606; A61M 39/06; Y10T 29/4987
See application file for complete search history.

(56) References Cited

U.S. PATENT DOCUMENTS 4,512,766 A * 4/1985 Vailancourt ........... A61M 39/14
                                                    251/149.1
4,613,956 A * 9/1986 Paterson ............... H01L 29/511
                                                    257/315
(Continued)

FOREIGN PATENT DOCUMENTS

CA       2133053       3/1995
CN       1053748       8/1991
(Continued)

OTHER PUBLICATIONS

International Search Report from related International Patent Applicaton No. PCT/US2011/033753 dated Dec. 29, 2011.
(Continued)

*Primary Examiner* — Bradley J Osinski
(74) *Attorney, Agent, or Firm* — Louis Woo

(57) ABSTRACT

A catheter assembly includes a catheter hub defining an interior cavity and a catheter tube extending distally thereof. A rigid actuator is positioned to extend proximally in the interior cavity and support a seal member positioned thereon in the interior cavity. The seal member includes a central membrane, a distal portion, and a proximal portion. An hourglass shaped actuator cavity is formed in the distal portion and receives a barbed end of the actuator. The outer surface of the seal member is in partial circumferential engagement with the catheter hub to define an air path that allows fluid communication between areas of the interior cavity distal and proximal of the seal member. The seal member may be configured for multi-use and include a
(Continued)

biasing member that moves the seal member to force the membrane back over the actuator to close the membrane.

17 Claims, 12 Drawing Sheets

Related U.S. Application Data continuation of application No. 14/169,892, filed on Jan. 31, 2014, now Pat. No. 9,399,116, which is a division of application No. 13/023,213, filed on Feb. 8, 2011, now Pat. No. 8,652,104, which is a continuation-in-part of application No. 12/823,656, filed on Jun. 25, 2010, now Pat. No. 9,545,495.

(52) U.S. Cl.
CPC .... *A61M 25/0102* (2013.01); *A61M 25/0606* (2013.01); *A61M 25/0618* (2013.01); *A61M 25/0693* (2013.01); *Y10T 29/4987* (2015.01); *Y10T 29/49826* (2015.01); *Y10T 29/49872* (2015.01)

(56) References Cited

U.S. PATENT DOCUMENTS

| | | |
|---|---|---|
| 5,419,766 A | 5/1995 | Chang et al. |
| 5,456,675 A | 10/1995 | Wolbring et al. |
| 5,458,640 A | 10/1995 | Gerrone |
| 5,509,912 A | 4/1996 | Vaillancourt et al. |
| 5,514,116 A | 5/1996 | Vaillancourt et al. |
| 5,575,769 A | 11/1996 | Vaillancourt |
| 5,685,866 A | 11/1997 | Lopez |
| 5,704,914 A | 1/1998 | Stocking et al. |
| 5,738,663 A | 4/1998 | Lopez |
| 5,810,780 A | 9/1998 | Brimhall et al. |
| 5,817,069 A | 10/1998 | Arnett |
| 5,820,596 A | 10/1998 | Rosen et al. |
| 5,830,189 A | 11/1998 | Chang |
| 5,833,662 A | 11/1998 | Stevens |
| 5,839,715 A | 11/1998 | Leinsing |
| 5,843,046 A | 12/1998 | Motisi et al. |
| 5,871,500 A | 2/1999 | Jepson et al. |
| 5,911,710 A | 6/1999 | Barry et al. |
| 5,954,691 A | 9/1999 | Prosl |
| 5,954,698 A | 9/1999 | Pike |
| 5,967,490 A | 10/1999 | Pike |
| 6,165,168 A | 12/2000 | Russo |
| 6,171,287 B1 | 1/2001 | Lynn et al. |
| 6,213,978 B1 | 4/2001 | Voyten |
| 6,224,569 B1 | 5/2001 | Brimhall |
| 6,228,065 B1 | 5/2001 | Brimhall |
| 6,261,272 B1 | 7/2001 | Gross et al. |
| 6,322,537 B1 | 11/2001 | Chang |
| 6,485,473 B1 | 11/2002 | Lynn |
| 6,506,181 B2 | 1/2003 | Meng et al. |
| 6,699,221 B2 | 3/2004 | Vaillancourt |
| 6,719,726 B2 | 4/2004 | Meng et al. |
| 6,808,161 B1 | 10/2004 | Hishikawa |
| 7,001,774 B1 | 2/2006 | Gamble et al. |
| 7,008,404 B2 | 3/2006 | Nakajima |
| 7,294,296 B2 | 11/2007 | Davey |
| 7,306,199 B2 | 12/2007 | Leinsing et al. |
| 7,347,839 B2 | 3/2008 | Hiejima |
| 7,470,261 B2 | 12/2008 | Lynn |
| 7,578,803 B2 | 8/2009 | Rome et al. |
| 7,854,731 B2 | 12/2010 | Rome et al. |
| 8,152,774 B2 | 4/2012 | Pasqualucci |
| 8,652,104 B2 | 2/2014 | Goral |
| 2002/0128604 A1 | 9/2002 | Nakajima |
| 2004/0106903 A1 | 6/2004 | Shue et al. |
| 2004/0127853 A1 | 7/2004 | Howell |
| 2004/0138626 A1 | 7/2004 | Cote, Sr. et al. |
| 2004/0199143 A1 | 10/2004 | Lauer |
| 2004/0225260 A1 | 11/2004 | Villa et al. |
| 2005/0085789 A1 | 4/2005 | Khan et al. |
| 2005/0096596 A1 | 5/2005 | Crawford et al. |
| 2005/0159705 A1 | 7/2005 | Crawford et al. |
| 2005/0273076 A1 | 12/2005 | Beasley et al. |
| 2005/0288634 A1 | 12/2005 | O'Heeron et al. |
| 2006/0155245 A1 | 7/2006 | Woehr |
| 2006/0264834 A1 | 11/2006 | Vaillancourt |
| 2007/0016141 A1 | 1/2007 | Saito et al. |
| 2007/0016167 A1 | 1/2007 | Smith et al. |
| 2007/0083162 A1 | 4/2007 | O'Reagan et al. |
| 2007/0093778 A1 | 4/2007 | Cindrich et al. |
| 2007/0112305 A1 | 5/2007 | Brimhall |
| 2007/0191775 A1* | 8/2007 | Diep ............... A61M 39/0606 604/164.01 |
| 2007/0196414 A1 | 8/2007 | Hammarsten et al. |
| 2007/0233007 A1 | 10/2007 | Adams |
| 2007/0250037 A1 | 10/2007 | Brimhall et al. |
| 2008/0108944 A1 | 5/2008 | Woehr |
| 2008/0140021 A1 | 6/2008 | Richmond |
| 2009/0069757 A1 | 3/2009 | Muri et al. |
| 2010/0204648 A1 | 8/2010 | Stout et al. |
| 2010/0204660 A1 | 8/2010 | Mckinnon et al. |
| 2011/0046570 A1 | 2/2011 | Stout et al. |
| 2011/0160662 A1 | 6/2011 | Stout et al. |
| 2011/0160663 A1 | 6/2011 | Stout et al. |
| 2011/0213307 A1 | 9/2011 | Kawai et al. |

FOREIGN PATENT DOCUMENTS

| | | |
|---|---|---|
| CN | 1285758 | 8/1991 |
| CN | 1285758 | 2/2001 |
| CN | 1319023 | 10/2001 |
| DE | 03000903 | 7/1981 |
| DE | 03100622 | 2/1982 |
| DE | 29901139 | 4/1999 |
| DE | 202006017732 | 3/2007 |
| EP | 0414997 | 3/1991 |
| EP | 0471547 | 2/1992 |
| EP | 1240916 | 9/2002 |
| EP | 1378263 | 1/2004 |
| EP | 1457225 | 9/2004 |
| EP | 1457229 | 9/2004 |
| EP | 1611916 | 1/2006 |
| EP | 1946791 | 7/2008 |
| JP | 2002263197 | 9/2002 |
| JP | 2002537953 | 11/2002 |
| JP | 2004244169 | 9/2004 |
| JP | 2005087574 | 4/2005 |
| JP | 2007508854 | 4/2007 |
| JP | 2007510502 | 4/2007 |
| JP | 2008173206 | 7/2008 |
| JP | 2009527286 | 7/2009 |
| JP | 2009553418 | 11/2009 |
| JP | 2010504823 | 2/2010 |
| JP | 2010508905 | 3/2010 |
| JP | 2012517326 | 8/2012 |
| WO | 2008042285 | 4/2008 |
| WO | 2010038471 | 4/2010 |
| WO | 2010093791 | 8/2010 |

OTHER PUBLICATIONS

International Written Opinion from related International Patent Applicaton No. PCT/US2011/033753 dated Dec. 29, 2011.
International Preliminary Report on Patentability from related International Patent Applicaton No. PCT/US2011/033753 dated Dec. 28, 2012.
Non-Final Office Action dated Jun. 5, 2013 in U.S. Appl. No. 13/023,213.
Restriction Requirement dated Aug. 21, 2013 in U.S. Appl. No. 12/823,656.
Final Office Action dated Sep. 25, 2013 in U.S. Appl. No. 13/023,213.
Notice of Allowance dated Oct. 17, 2013 in U.S. Appl. No. 13/023,213.
Extended European Search Report and Opinion from the EPO for EP Application No. 14156041.7 dated Mar. 20, 2014 (7 pages).

(56) References Cited

OTHER PUBLICATIONS

Extended European Search Report and Opinion from the EPO for EP Application No. EP 14156037 (Communication dated Mar. 27, 2014) (5 pages).
Extended European Search Report and Opinion from the EPO for EP Application No. EP 14156034 (Communication dated Mar. 27, 2014) (6 pages).
Extended European Search Report and Opinion from the EPO for EP Application No. 14156032.6 dated Mar. 27, 2014.
Eurpoean Search Report and Opiniond dated Jun. 4, 2014 from EPO for 14156040.9.
Office Action dated Jun. 16, 2014 in CN Application No. 201180031608.
USPTO; Non-Final Office Action dated Jul. 29, 2014 in U.S. Appl. No. 14/057,589.
European Patent Office, European Search Report issued in Application No. 14173938.3 dated Oct. 15, 2014.
Office action dated Oct. 22, 2014 in Australian Application No. 2011269819.
Office Action dated Dec. 2, 2014 in CN Application No. 201180031608.
Office Action dated Jan. 13, 2015 in JP Application No. 20130516572.
USPTO; Non-Final Office Action dated Jan. 29, 2015 in U.S. Appl. No. 12/823,656.
Notice of Acceptance dated May 18, 2015 in Australian Application No. 2011269819.
Notice of Allowance dated Jul. 10, 2015 in CN Application No. 201180031608.
Notice of Allowance dated Aug. 27, 2015 in JP Application No. 2013516572.
USPTO; Final Office Action dated Sep. 17, 2015 in U.S. Appl. No. 12/823,565.
Office Action dated Sep. 23, 2015 in KR Application No. 10-2013-7002162.
USPTO; Non-Final Office Action dated Oct. 8, 2015 in U.S. Appl. No. 14/169,892.
Extended European Search Report and Opinion from the EPO for EP Application No. 15172829 dated Oct. 12, 2015.
Office Action dated Nov. 10, 2015 in European Application No. 14156040.9.
Office Action dated Nov. 10, 2015 in European Application No. 14156041.7.
Office Action dated Nov. 19, 2015 in U.S. Appl. No. 14/057,589.
Notice of Allowance dated Jan. 5, 2016 in Canadian Application No. 2,797,083.
Decisioin to Grant dated Feb. 18, 2016 in EP Application No. 14156041.7.
Office Action dated Mar. 8, 2016 in EP Application No. 14173938.3.
Office Action dated Apr. 21, 2016 in Australian Application No. 2015203793.
Notice of Allowance dated Apr. 27, 2016 in Korean Application No. 10-2013-7002162.
Notice of Allowance dated Apr. 29, 2016 in U.S. Appl. No. 14/169,892.
Notice of Acceptance dated Jun. 14, 2016 in Australian Application No. 2015203793.
Final Office Action dated Jun. 24, 2016 in U.S. Appl. No. 12/823,656.
Notice of Allowance dated Jun. 30, 2016 in EP Application No. 14173938.3.
Office Action dated Jul. 7, 2016 in European Application No. 15172829.2.
Notice of Allowance dated Jul. 29, 2016 in JP Application No. 20150193443.
Notice of Allowance dated Aug. 9, 2016 in JP Application No. 2015-193440.
Notice of Allowance dated Aug. 9, 2016 in JP Application No. 2015-193442.
Office Action dated Aug. 15, 2016 in Japanese Application No. 2015-193440.
Office Action dated Aug. 15, 2016 in Japanese Application No. 2015-193441.
Notice of Allowance dated Aug. 22, 2016 in Japanese Application No. 2015-193442.
Office action dated Aug. 29, 2016 in JP Application No. 20150193444.
Office Action dated Sep. 5, 2016 in Japanese Application No. 2015-193444.
Notice of Allowance dated Oct. 7, 2016 in EP Application No. 15172829.2.
USPTO; Notice of Allowance dated Oct. 21, 2016 in U.S. Appl. No. 12/823,656.
Office action dated Dec. 17, 2018 in JP Patent Application No. 2018-009588.
Office action dated Jan. 4, 2019 in CA Application No. 2993693.
Office action dated Feb. 6, 2019 in AU Application No. 2018200782.
Notice of Allowance dated Jul. 1, 2019 in JP Application No. 2018-009588.
CIPO; Office Action dated Sep. 5, 2019 in CA Application No. 2993693.
USPTO; Non-Final Office Action dated May 1, 2020 in U.S. Appl. No. 16/110,051.
CIPO; Notice of Allowance dated Jun. 19, 2020 in CA Application No. 2993693.
USPTO; Non-Final Office Action dated Jul. 1, 2020 in U.S. Appl. No. 16/880,633.
USPTO; Final Office Action dated Aug. 10, 2020 in U.S. Appl. No. 16/110,051.

* cited by examiner

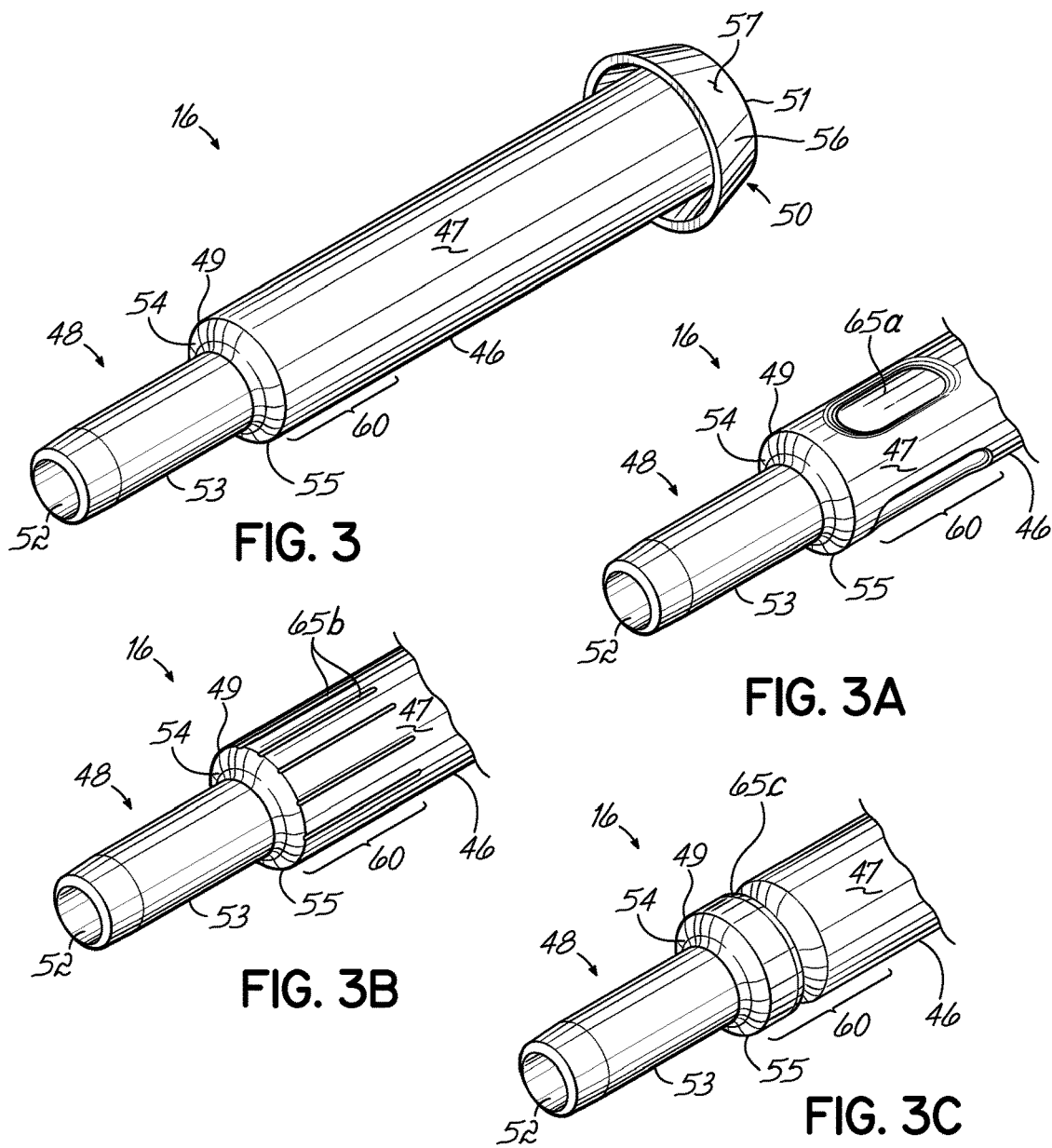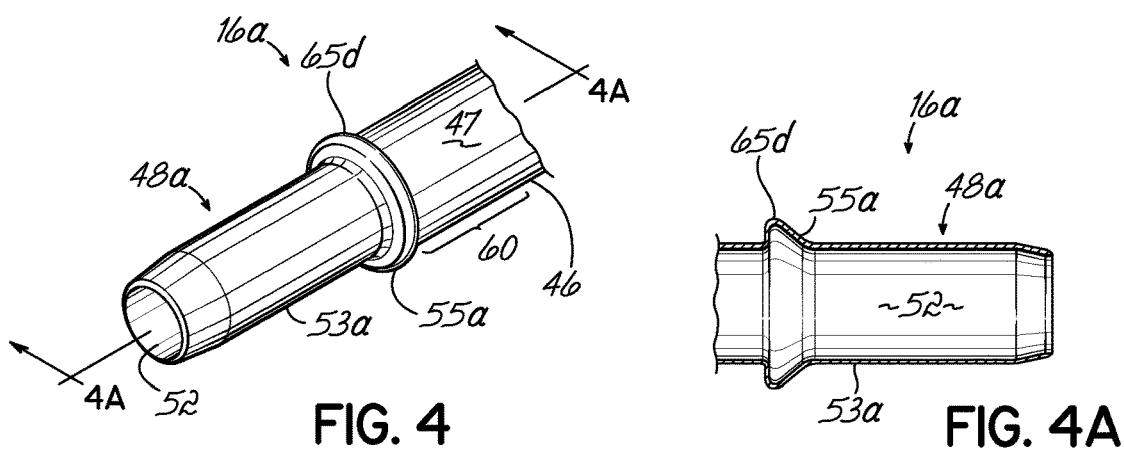

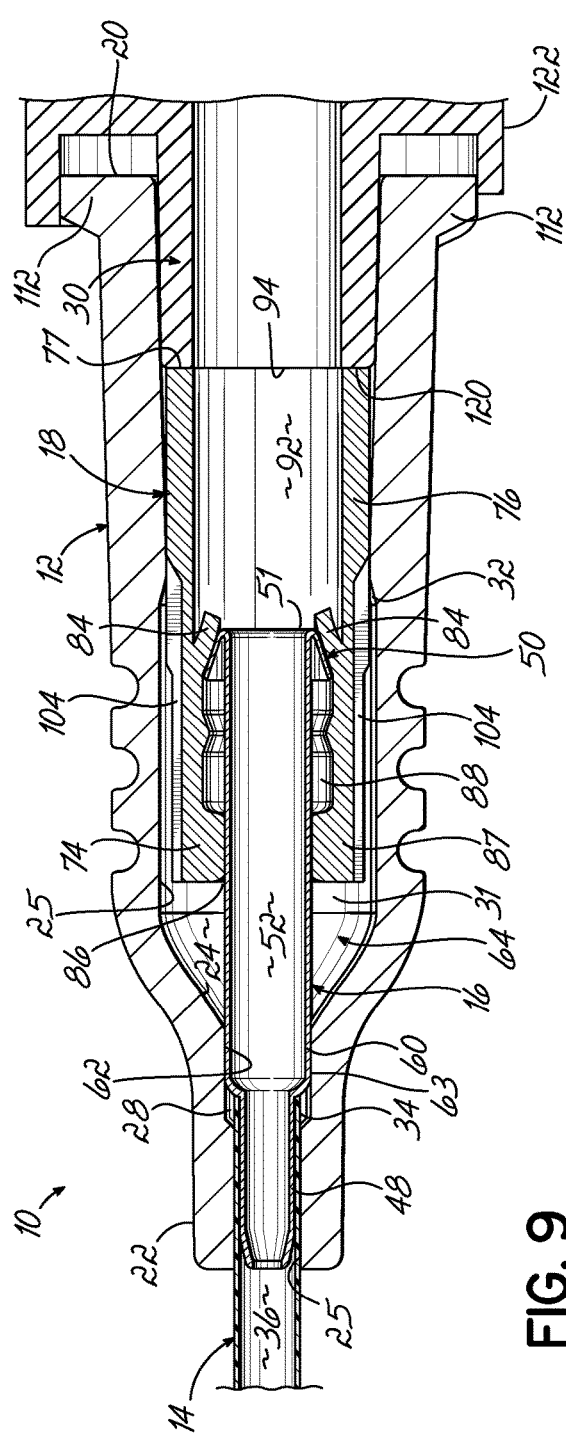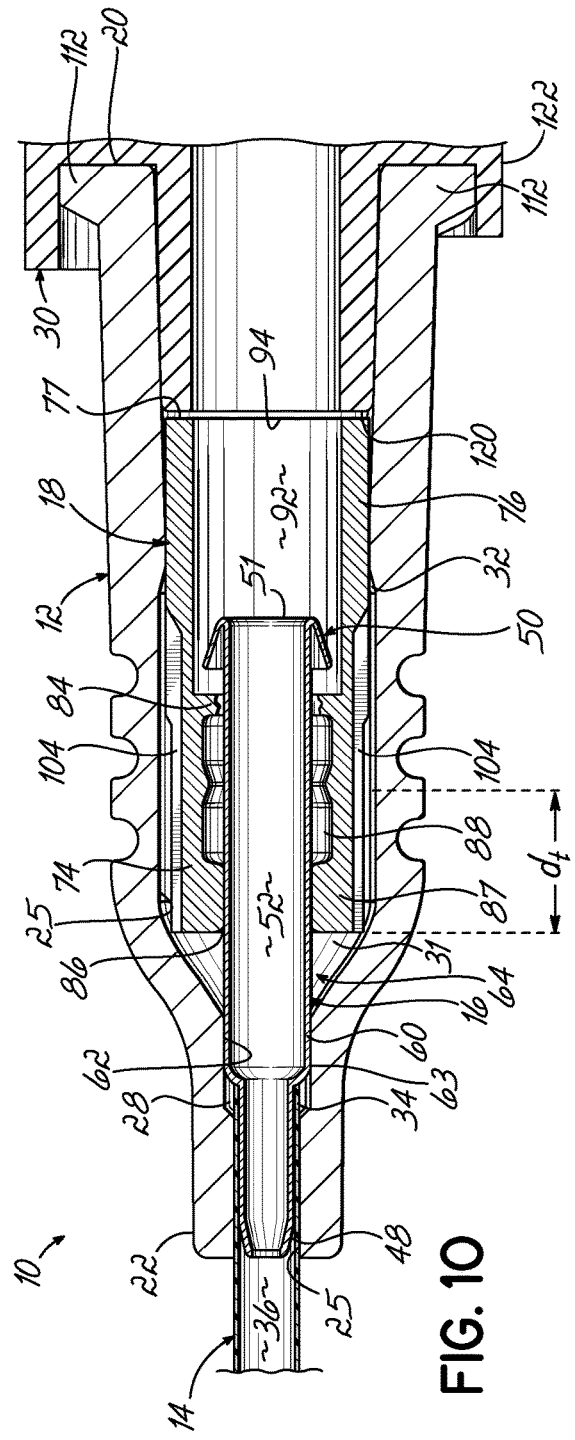

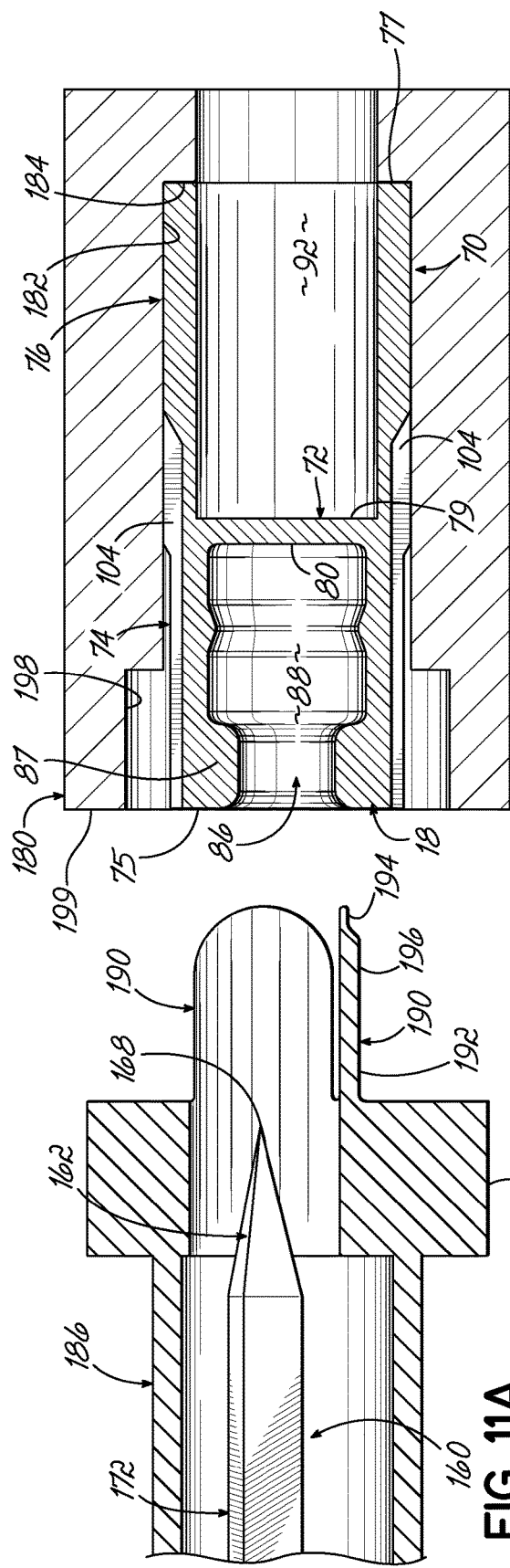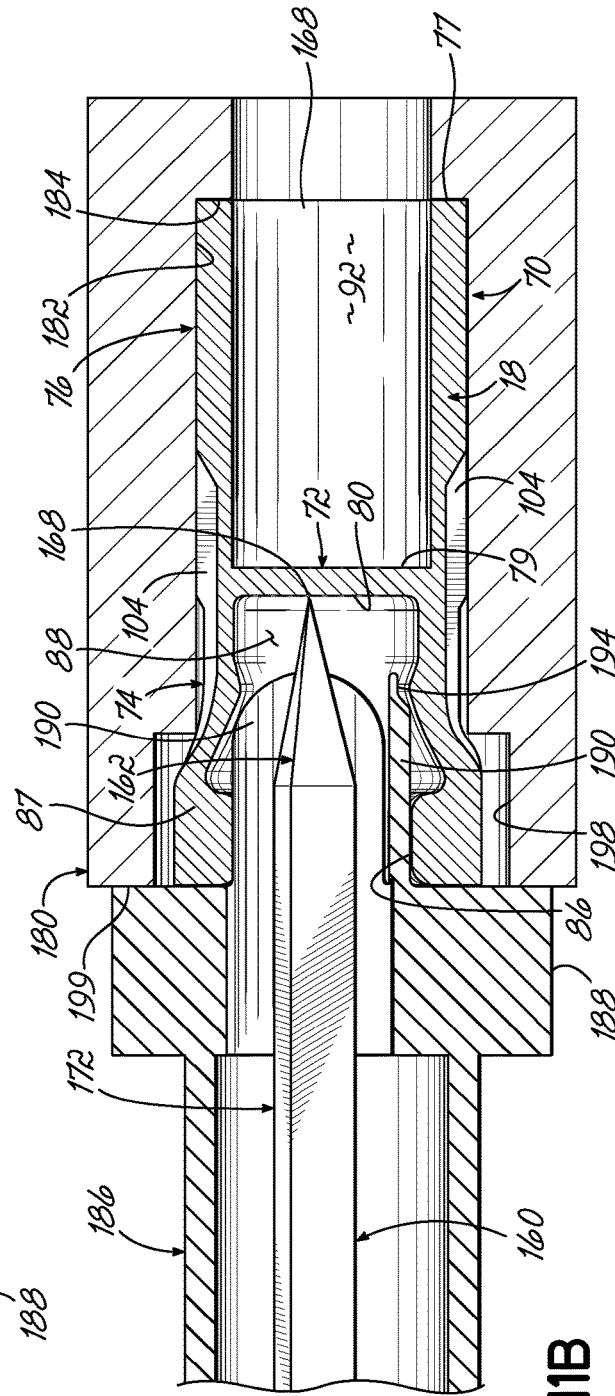
FIG. 11A
FIG. 11B

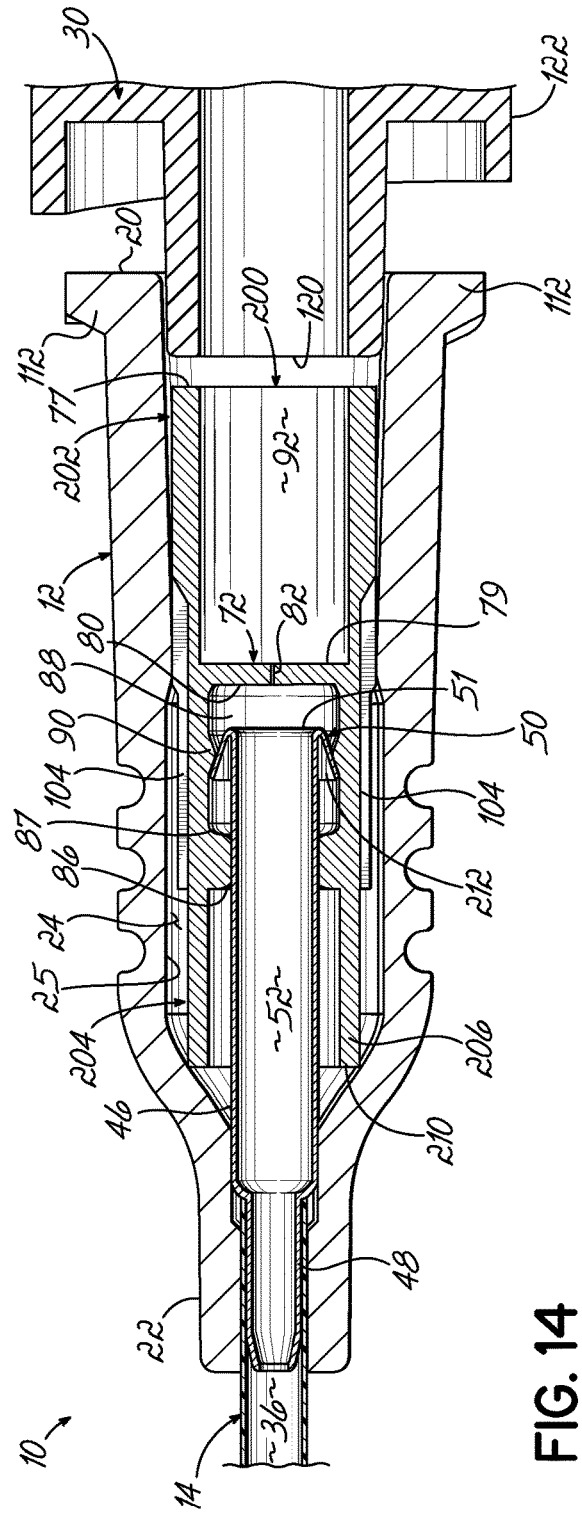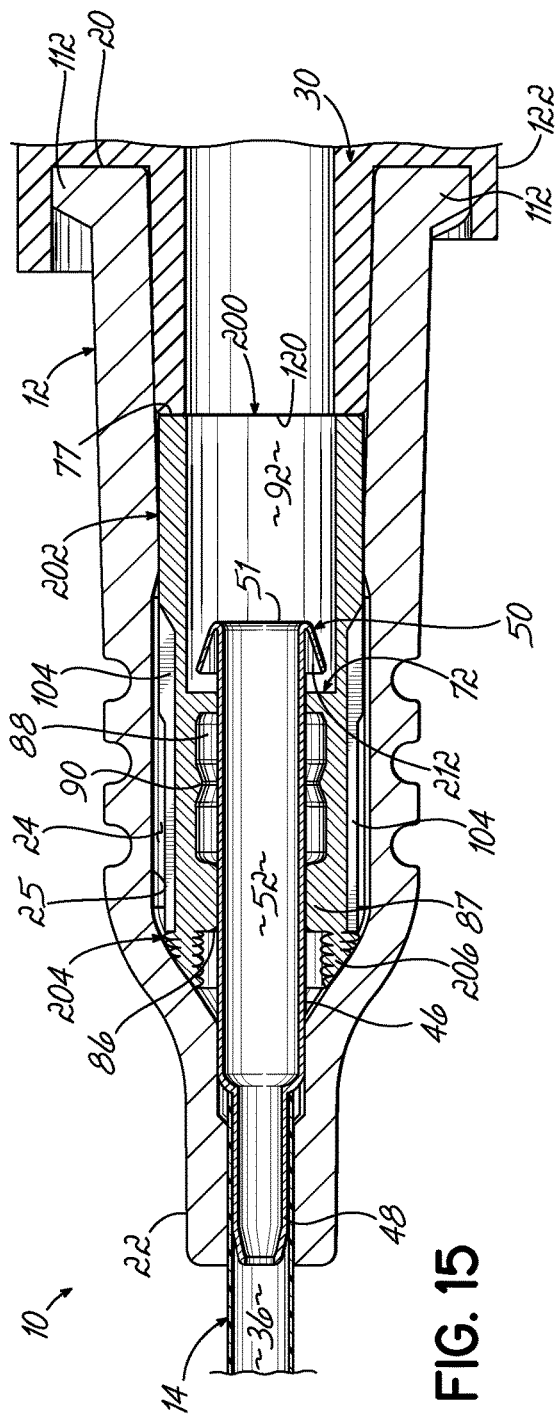
FIG. 14
FIG. 15

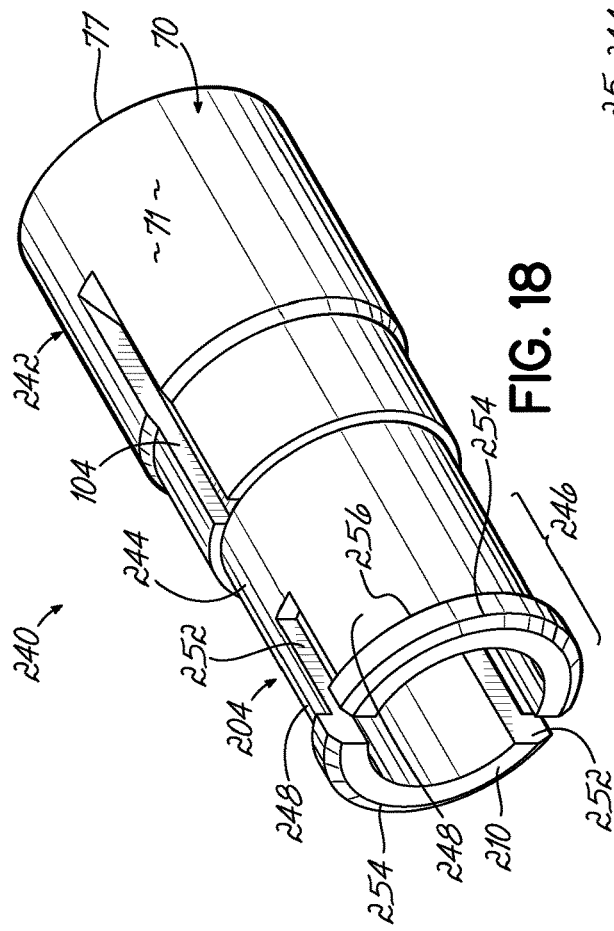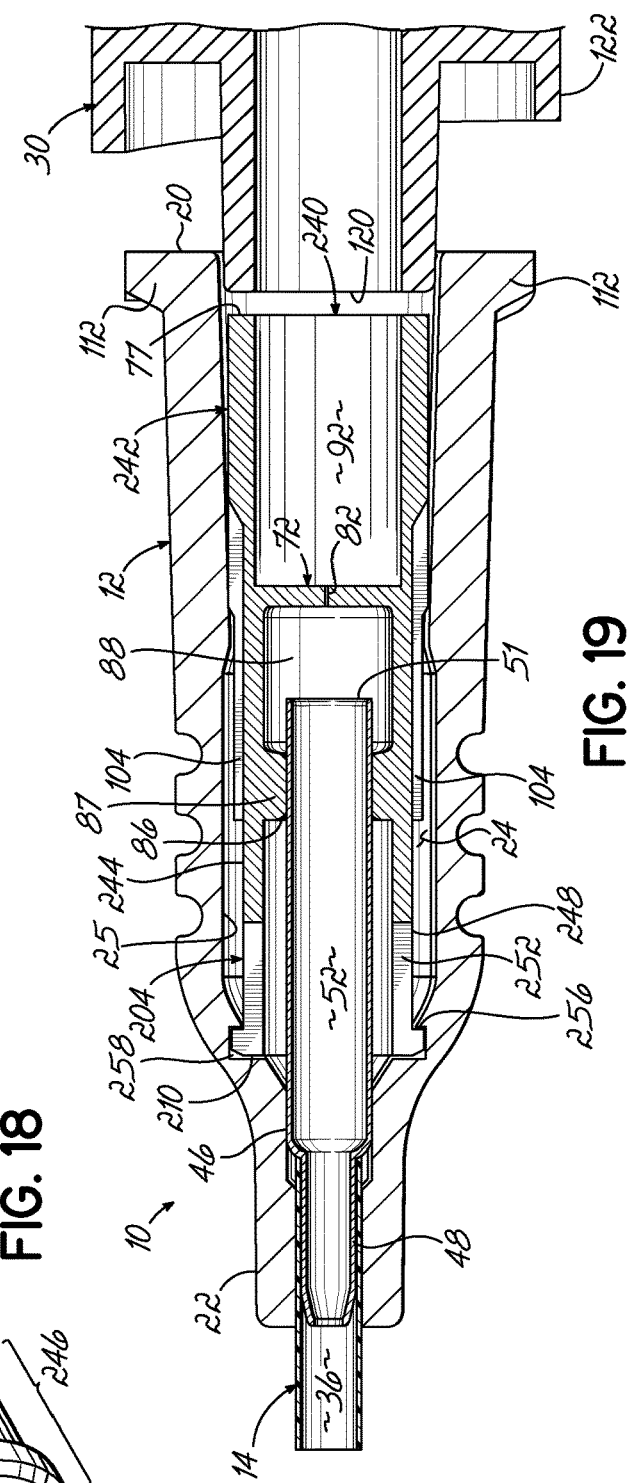

CATHETER ASSEMBLY WITH SEAL MEMBER

CROSS REFERENCE TO RELATED APPLICATION

This application is a continuation of, claims priority to and the benefit of U.S. Ser. No. 15/190,017 filed Jun. 22, 2016 and entitled "METHOD OF MAKING CATHETER ASSEMBLY WITH SEAL MEMBER." The '017 application is a continuation of, claims priority to and the benefit of U.S. Ser. No. 14/169,892 filed Jan. 31, 2014 and entitled "METHOD OF MAKING CATHETER ASSEMBLY WITH SEAL MEMBER," which issued as U.S. Pat. No. 9,399,116 on Jul. 26, 2016. The '892 application is a divisional of, claims priority to and the benefit of U.S. Ser. No. 13/023,213 filed Feb. 8, 2011 and entitled "CATHETER ASSEMBLY WITH SEAL MEMBER," which issued as U.S. Pat. No. 8,652,104 on Feb. 18, 2014. The '104 patent is a continuation-in-part of, claims priority to and the benefit of U.S. Ser. No. 12/823,656 filed Jun. 25, 2010 and entitled "CATHETER ASSEMBLY WITH SEAL MEMBER," which issued as U.S. Pat. No. 9,545,495 on Jan. 17, 2017. All of the aforementioned applications are incorporated herein by reference in their entirety.

TECHNICAL FIELD

The present invention relates to over-the-needle catheters such as peripheral intravascular catheters or PIVC's and, more particularly, to a catheter assembly used with such catheters having a seal disposed in a hub thereof for enhanced blood control.

BACKGROUND

By way of background, conventional PIVC's include a catheter assembly, typically having a catheter hub and a catheter tube extending distally thereof, and a needle assembly mounted together in an over-the-needle fashion. The needle assembly typically includes a needle hub or support and a needle cannula extending distally thereof and, in a ready position of the PIVC, extending through the catheter tube to expose a sharp tip thereof distal of the tube and used to penetrate tissue for insertion of the catheter tube within the vascular system of a patient. Once the catheter tube is disposed within the vasculature, the needle cannula is withdrawn proximally from the catheter assembly and the catheter assembly remains in fluid communication with the vasculature. The PIVC may also include a protector to enclose at least the tip of the needle cannula, if not the entire cannula, after use. A PIVC with a protector may be referred to as a safety catheter.

The catheter hub typically has an open proximal end adapted to receive a male luer taper into the interior cavity of the catheter to establish a fluid connection between the patient's vasculature and the luer taper. The proximal end may also be provided with external ears or the like to secure the luer taper in the catheter hub, such as when the luer taper is coupled with a male luer lock collar or nut to form part of a male luer lock such as of a connector of an administration set or the end of a syringe, or the like. Under normal conditions, after withdrawal of the needle cannula and before a luer taper is inserted into the catheter hub, blood immediately starts flowing through the catheter tube and into the interior cavity of the catheter hub. In typical catheter hub designs, the proximal end of the catheter hub is in open communication with the catheter tube through the interior cavity such that, if not attended to in a timely manner, blood can flow into the catheter hub and spill into the surrounding environment. To limit blood flow into the catheter hub, medical personnel typically apply digital pressure near the insertion site to occlude blood flow into the catheter tube. An administration set or a syringe is then coupled to the catheter assembly for introducing fluids into, and/or withdrawing blood from, the patient.

Various designs of catheter assemblies have been proposed for controlling or limiting blood flow by inclusion of a hemostasis seal within the interior cavity or at the proximal end opening of the catheter hub, to block fluid flow between the proximal end of the catheter hub and the catheter tube. In these designs, the hemostasis seal provides for passage of the needle cannula therethrough in the ready position of the PIVC, but seals against the flow of blood to or out of the proximal end of the catheter hub upon proximal withdrawal of the needle cannula. The hemostasis seal is adapted to be opened by insertion of a luer taper into the catheter hub to allow flow of fluid between the luer taper and the catheter tube.

While various designs of catheter assemblies with hemostasis seals have been proposed, none seems to have garnered commercial acceptance. Thus, improvements are considered necessary in order to address drawbacks of existing proposals.

SUMMARY

The present invention provides catheter assemblies with improved hemostasis seal arrangements which are aimed at addressing drawbacks of previously proposed catheter assembly designs. To that end, and in accordance with one feature of the present invention, a rigid actuator extends proximally in the interior cavity from the catheter hub distal end to a free end having an enlarged proximal flange. The enlarged proximal flange may advantageously define a barb. In accordance with a further feature of the present invention, a seal member is disposed in the interior cavity of the catheter hub including a membrane and a distal portion extending distally from the membrane to a sealing outlet bore with the distal portion having an actuator cavity formed between the membrane and the sealing outlet bore so as to receive the free end of the actuator therein through the sealing outlet bore. The actuator cavity may advantageously have a narrowed portion that defines an hourglass shape thereto such that with the actuator extending through the sealing outlet bore into the actuator cavity, a surface of the proximal flange engages against the narrowed portion of the actuator cavity. The foregoing features provide a reliable seal between the seal member and the actuator while also providing a reliable hold of the seal member to the actuator.

The seal member advantageously includes a proximal portion, such as a cylinder, extending proximally from the membrane to a proximal end defining an impact surface against which a free or distal end of a male luer taper impacts upon insertion into the catheter hub interior cavity to thereby cause the seal member to slide axially along the actuator. The membrane is eventually forced open as the free end of the actuator passes through the membrane, which may advantageously be slit to facilitate the opening of the membrane. The seal member is advantageously a unitary member.

In accordance with another feature of the present invention, the actuator for the catheter assembly may include an eyelet portion adapted to help secure the catheter tube to the catheter hub, such that the actuator is an integral part of the eyelet. To that end, the actuator may include a main shaft having a first cross dimension, an eyelet portion at one end thereof having an eyelet shaft of a second cross dimension, with the barb at an opposite end thereof having a third cross dimension. The third cross dimension is larger than the first and second cross dimensions, with the second cross dimension being equal to or smaller than the first cross dimension and advantageously being sized in relation to the gauge of the needle cannula to be used therewith. The actuator thus provides the dual functionality of securement of the catheter tube to the catheter hub and opening of the seal member as desired.

In accordance with a yet further feature of the present invention, where the needle cannula gauge is small, such as 16 or 18 gauge wherein the needle cannula diameter is quite large, the cross dimension of the eyelet shaft may be nearly the same size or slightly smaller than the cross dimension of the actuator main shaft. The actuator is advantageously provided with a surface feature in the form of a radially outwardly extending annular rib to enhance securement of the actuator to the catheter hub. The annular rib may be at the junction of the main and eyelet shafts. For larger gauge needle cannula, such as 20, 22, 24, and/or 26 gauges wherein the needle cannula diameter is relatively small, the eyelet shaft cross dimension may be substantially smaller than the main shaft cross dimension. If desired, the actuator may be provided with a surface feature to enhance securement of the actuator to the catheter hub. The surface feature may be an annular rib, or may be one or more dimples or one or more axial or annular grooves in the main shaft adjacent the eyelet shaft.

The seal member may be supported on the actuator with an outer surface of the seal member in partial circumferential engagement with the catheter hub inner surface or wall such that an air path is maintained between areas of the interior cavity both distal and proximal of the seal member. The seal member is thus held against undue sideways or similar movement or tilting, while allowing escape of air or other fluid to facilitate movement of the seal member sliding axially along the actuator. The air path or at least a portion thereof which serves to limit the circumferential engagement to a partial circumferential engagement, may advantageously be defined at least in part by an axial channel or groove in the outer surface of the seal member, wherein the seal member is not in engagement with the inner wall of the catheter hub in the area of the groove. The aspects of the seal member proximal and distal the area of the partial circumferential engagement may be sized with a cross dimension smaller than the cross dimension of the confronting areas of the catheter hub so as to form annular gaps therebetween which may also define part of the air path.

The catheter assembly may be configured to be used with a needle cannula and a nose that projects into the interior cavity of the catheter hub. The nose advantageously has a standard luer taper proximal portion to engage with the catheter hub inner wall adjacent the proximal opening of the catheter hub and a distal aspect sized smaller than the standard luer portion so as to project into the proximal cylindrical portion of the seal member with a distal end of the nose being adjacent the membrane of the seal member. The membrane may have a slit therethrough that defines slit flaps. The distal end of the nose may advantageously include a recessed bore that overlies the slit in the membrane. The bore is configured to receive the slit flaps during withdrawal of the needle cannula from the catheter hub.

In a further aspect of the present invention, the seal member may be disposed in the catheter hub such that the distal end of the seal member supporting the sealing outlet bore is spaced a first distance from the distal end of the catheter hub and the impact end of the seal member is spaced a second distance from the proximal end of the catheter hub, with the seal member being axially shifted, such as by the male luer taper inserted into the catheter hub, a third distance to force the membrane over the free end of the actuator to open the seal member. Advantageously, the third distance is less than the first distance such that the seal member is not axially compressed after being axially shifted the third distance to open the seal membrane. In any event, the proximal portion of the seal member is such that it is not axially compressed after the sealing member has been moved to the open condition. Further advantageously, the first and second distances are each substantially larger than the axial thickness of the seal member membrane.

The slit of the membrane, where provided, is advantageously a tri-slit so as to form a Y-shape when seen in plan view. In accordance with a yet further aspect of the present invention, a punch tool for forming a tri-slit in the membrane of the seal member includes a three-sided pyramid having a base at one end with three corners and a pointed tip at an opposed end, and a shaft extending from the base and having three straight, sharpened edges and generally planar lands between respective pairs of edges, with each of the edges being generally axially aligned with a respective one of the three corners of the base. An associated method includes inserting the seal member in a bore of a fixture, inserting the punch tool into the fixture to engage the membrane, and continuing to insert the punch tool into the fixture to push at least a portion of the pyramid of the punch tool through the membrane.

In still a further aspect of the present invention, the seal member may be configured as a multi-use seal including a biasing member between the sealing outlet bore and the distal end of the catheter hub. In this embodiment, the seal member is axially shiftable along the actuator in a distal direction to force the membrane over the free end of the actuator and open the membrane. The biasing member is configured to axially shift the seal member along the actuator in a proximal direction to force the membrane back over the free end of the actuator and close the membrane. For example, when the male luer taper is removed from the catheter hub, the biasing member is then able to axially shift the seal member toward the closed position. Thus, the biasing member allows the seal member to be repeatedly opened and closed.

In one embodiment, the biasing member may include a tubular extension member capable of being compressed when the seal member is opened to thereby provide the return force that axially shifts the seal member toward the closed position. Alternatively, the biasing member may include one or more legs having a similar capability. In a further aspect in accordance with the invention, the biasing member may be partially compressed when the membrane is closed to increase the return force acting on the seal member as the membrane is passed back over the free end of the actuator. In another aspect, the biasing member may include a flange configured to cooperate with an annular rib in the catheter hub to secure or enhance securement of the seal member therein. By virtue of the foregoing, individually and in combination, there are provided catheter assemblies with improved hemostasis seal arrangements which are aimed at addressing drawbacks of previously proposed catheter assembly designs. These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the invention and, together with the general description given above and the detailed description of the embodiments given below, serve to explain the principles of the invention.

FIG. 3 is a perspective view of the actuator of FIGS. 1 and 2;

FIGS. 3A-3C are partial, perspective views showing alternative embodiments of the actuator of FIGS. 1 and 2 for purposes of explaining a yet further feature of the present invention;

FIG. 4 is a partial, perspective view of an alternate embodiment of an actuator for the catheter assembly of FIGS. 1 and 2;

FIG. 4A is a cross-sectional view taken along line 4A-4A of FIG. 4;

FIG. 9 is a partial, cross-sectional view of the catheter assembly of FIG. 1 as the seal member is being actuated to slide axially along the actuator by insertion of a male luer taper into the catheter hub;

FIG. 10 is a partial, cross-sectional view of the catheter assembly of FIG. 1 after the seal member has been slid axially over the free end of the actuator to be fully opened by insertion of the male luer taper into the catheter hub;

FIG. 11A is a view of an alternative embodiment showing the seal member of FIG. 1, and a fixture in cross section, and a spreader tool for use therewith for forming the tri-slit in the membrane;

FIG. 11B is a view similar to FIG. 11A, but showing the spreader tool engaged with the seal member;

FIG. 14 is a partial, cross-sectional view of a catheter assembly having the multi-use seal member of FIG. 13 prior to being actuated by insertion of a male luer taper into the catheter hub;

FIG. 15 is a partial, cross-sectional view of the catheter assembly of FIG. 14 after the seal member has been slid axially over the free end of the actuator to be fully opened by insertion of the male luer taper into the catheter hub thereby compressing a biasing member of the seal;

FIG. 18 is a perspective view of yet another multi-use seal member; and

FIG. 19 is a partial, cross-sectional view of a catheter assembly having the multi-use seal member of FIG. 18 prior to being actuated by insertion of a male luer taper into the catheter hub.

DETAILED DESCRIPTION

Figure 1:
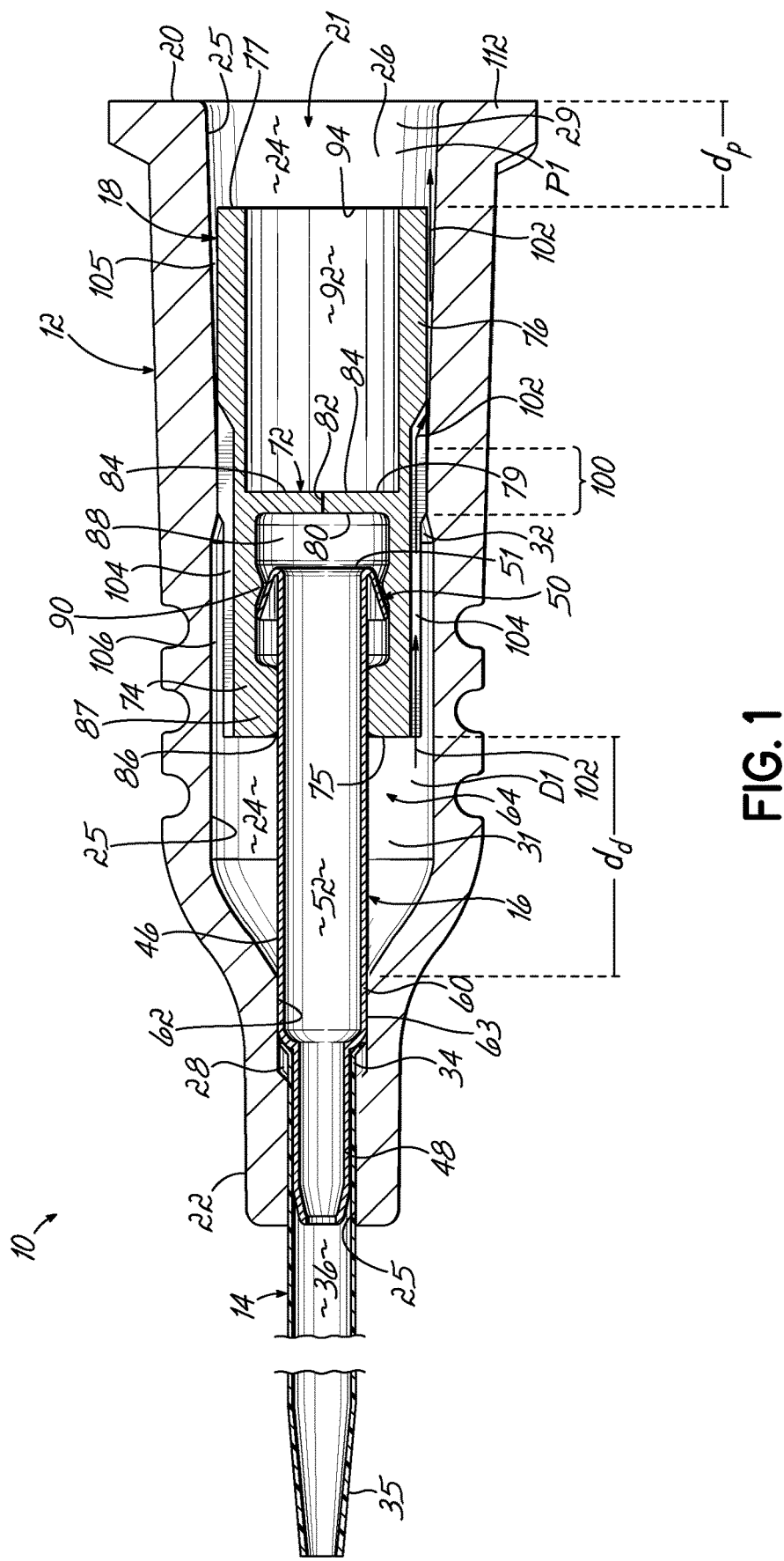
FIG. 1 is a cross-sectional view of one embodiment of a catheter assembly having an actuator and seal member in accordance with various features of the present invention.

In reference to FIG. 1, a catheter assembly 10 in accordance with various features of the present invention includes a catheter hub 12, a catheter tube 14 secured to and extending distally of the catheter hub 12, an actuator 16 secured to the catheter hub 12 and extending axially therewithin, and a seal member 18 disposed in the catheter hub 12 and movably supported on the actuator 16. The seal member 18 is axially shiftable relative to the actuator 16, such as by sliding axially therealong, between a closed or sealed position shown in FIG. 1 and an opened or actuated position (shown, for example, in FIG. 10). In the closed position, the catheter hub 12 is substantially sealed off from the catheter tube 14 such that blood flow into the catheter hub 12 is restricted. In the opened position, however, and as will be discussed in more detail below, the seal member 18 is pushed over the actuator 16 such that the catheter hub 12 and catheter tube 14 are in open fluid communication.

The catheter hub 12 includes a proximal end 20 with an unobstructed opening 21, a distal end 22, and an interior cavity 24 extending therebetween and defined by an inner surface or wall 25. The interior cavity 24 includes a proximal portion 26 extending from adjacent the proximal end 20 to near the distal end 22, and a distal cavity 28 adjacent distal end 22. The proximal portion 26 includes a first, upper section 29 which is shaped according to luer taper standards so as to matingly receive a luer taper 30 (FIGS. 9 and 10) therein, and a second, lower section 31 which has a relatively constant cross dimension (e.g., diameter) that is generally greater than at least the smallest, tapered cross dimension of the first section 29 with a transition region 32 being generally defined therebetween.

The catheter tube 14 includes a proximal end 34, a tapered distal end 35, and an open passageway 36 extending therebetween. The proximal end 34 of the catheter tube 14 is secured within the distal cavity 28 of the catheter hub 12 using the actuator 16 so that the catheter tube 14 extends distally of the catheter hub distal end 22. Thus, the actuator 16 not only supports the seal member 18 and facilitates its opening, but the actuator 16 also serves the function of securing the catheter tube 14 to the catheter hub 12.

Figure 2:
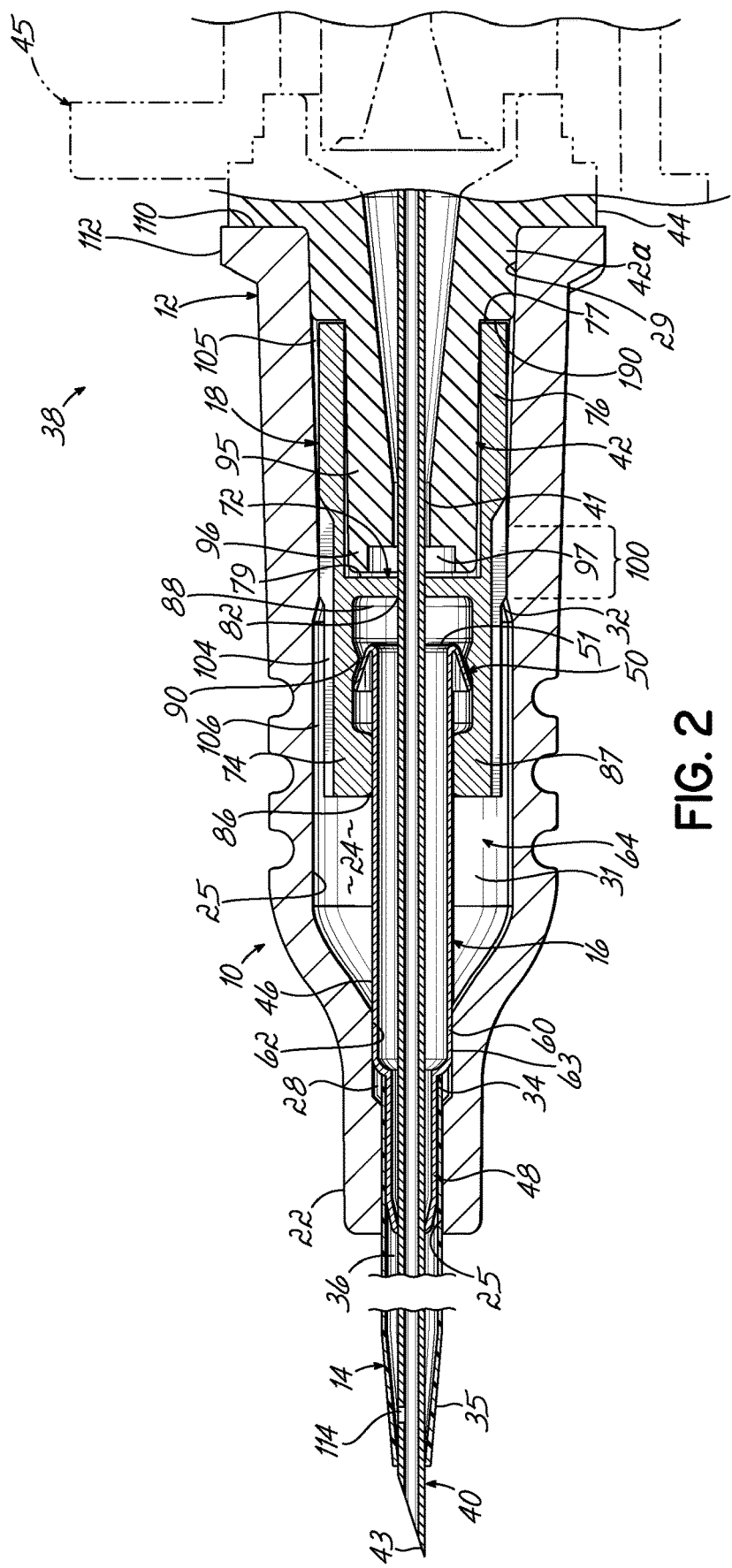
FIG. 2 is a partial, cross-sectional view of a PIVC including the catheter assembly of FIG. 1 and being in a ready position for purposes of explaining various features of the present invention.

Catheter assembly 10 is advantageously utilized as part of a PIVC 38, a portion of which is shown in FIG. 2 in a ready position of the PIVC 38. To that end, a needle cannula 40 has a shaft 41 and extends distally from a nose 42 to a sharp distal tip 43. The nose 42 extends into the upper section 29 of the interior cavity 24 of the catheter hub 12. In the ready position as shown in FIG. 2, the needle cannula 40 extends through the seal member 18, through the actuator 16, and through the catheter tube 14 so as to expose the sharp distal tip 43 beyond the distal end 35 of the catheter tube 14. In the embodiment shown in FIG. 2, the needle cannula 40 is axially slidable through the nose 42 such that the needle cannula 40 can be withdrawn proximally from the catheter tube 14 and the seal member 18 without necessarily proximally withdrawing the nose 42 from the catheter hub 12 until the needle cannula 40 is to be completely removed from the catheter assembly 10. Nose 42 may extend from a cap or flange 44 of a protector, one example of which is the needle guard housing 45 (only a portion of which is shown, in phantom, in FIG. 2) of a ProtectIV®PIVC available from Smiths Medical ASD, Inc. Other types of protectors (not shown) may be used with PIVC 38 as will be readily understood by those skilled in the art. As shown in FIG. 2, the flange 44 may abut the proximal end 20 of the catheter hub 12. Additionally, flange 44 may include an annular distal extension (not shown) that comes down around the proximal end 20 of the catheter hub 12 to facilitate securement of the PIVC 38 thereto, such as by interacting with the retaining ears 112 of catheter hub 12. In another embodiment (not shown), the nose and the needle cannula are secured together so as to move as one such that proximal withdrawal of the needle cannula necessarily also withdraws the nose from the catheter hub 12. In that embodiment, the nose serves as a needle hub or support for the needle cannula as exemplified by the JELCO®PIVC also available from Smiths Medical ASD, Inc. Other examples of needle cannula and nose combinations are shown in U.S. Patent Publication No. 2007/0191775, the disclosure of which is incorporated herein by reference in its entirety.

With further reference to FIG. 3, actuator 16 is generally rigid and includes a generally cylindrical main shaft 46 with an outer surface 47, a distal eyelet portion 48 at a distal end 49, and a proximal barb 50 at an opposite, proximal free end 51. An open passageway 52 extends between the free end 51 and the eyelet portion 48 to receive the needle cannula 40 therethrough, and for flow of fluid therethrough when the seal member 18 is in the opened position. The distal eyelet portion 48 is similar to a conventional eyelet and, for large gauge needle cannula 40, such as 20, 22, 24, and/or 26 gauge needle cannula 40, includes an eyelet shaft 53 and a head 54 that merges into the main shaft 46 at an intersection 55. The eyelet shaft 53 has a cross dimension that is substantially smaller than a cross dimension of the main shaft 46 so as to be closely sized to the diameter of the needle cannula 40. The barb 50 at the proximal free end 51 may be characterized by having a maximum cross dimension generally greater than the cross dimension of the main shaft 46 (and thus also of the eyelet shaft 53) and may include an enlarged flange 56 that essentially folds back over a portion of the main shaft 46 and diverges in a distal direction to define a frustoconical outer surface 57 that is radially outward of the main shaft 46.

As illustrated in FIG. 1, the distal eyelet portion 48 of actuator 16 is frictionally fit within the catheter hub distal end 22, such as in distal cavity 28, to secure the catheter tube 14 to the catheter hub 12. Unlike a conventional eyelet, however, the main shaft 46 of actuator 16 extends proximally from the catheter hub distal end 22 such that a distal portion 60 thereof frictionally engages with a portion 62 of the distal cavity 28 as at 63 to assist in securing the actuator 16 to the catheter hub 12, and further such that the proximal free end 51 is spaced from the distal end 22 but remains disposed within the interior cavity 24 of catheter hub 12. More particularly, the main shaft 46 of the actuator 16 extends out of the distal cavity 28 and into the proximal portion 26 of the interior cavity 24, but the proximal free end 51 of the actuator 16 does not extend to the proximal end 20 of the catheter hub 12 and instead terminates distally thereof. In the embodiment shown, for example, the proximal free end 51 terminates within the second section 31 of the interior cavity 24. Additionally, the radial cross dimension of the actuator 16, including, for example, the barb 50 thereof, is smaller than the cross dimension of the second section 31 of the interior cavity 24 proximal of distal cavity 28 so as to generally define an annular space 64 between the inner wall 25 of the catheter hub 12 and the actuator 16. As will be discussed in more detail below, the annular space 64 is configured to receive the seal member 18 as it is moved toward the opened position.

To enhance securement of the actuator 16 to the catheter hub distal end 22, the actuator 16 may include a surface feature formed thereon such as one or more dimples 65a in the outer surface 47 in the distal portion 60 of the main shaft 46 spaced near eyelet portion head 54 (FIG. 3A), one or more axial scribe lines or grooves 65b in the outer surface 47 extending along the distal portion 60 of the main shaft 46, and possibly into the eyelet portion 54 (FIG. 3B), or one or more annular grooves 65c in the outer surface 47 and along the distal portion 60 of the main shaft 46 (FIG. 3C). The surface feature is configured to interact with the catheter hub portion 62 as at 63 to increase frictional engagement therebetween.

The actuator 16 as shown in FIG. 3 is advantageously configured for small diameter needle cannula 40, such as gauges 20 through 26. Where the diameter of the needle cannula 40 is large, such as gauges 16 or 18, an alternative embodiment of actuator 16a may be provided as shown in FIG. 4 (where like numbers represent like features as in actuator 16). To that end, the eyelet shaft 53a of the eyelet portion 48a will have a cross dimension that is possibly the same as (such as for a 16 gauge needle cannula 40) or only slightly smaller than (for a 18 gauge needle cannula 40) the cross dimension of the main shaft 46. In that circumstance, securement of the actuator 16a may be enhanced by providing a surface feature to the actuator 16a in the form of a radially outwardly extending annular rib 65d which may provide a cross dimension about 12% larger than the cross dimension of the main shaft 46. Advantageously, rib 65d is in the form of a sawtooth in cross section (FIG. 4A), but it could also be more rounded. Annular rib 65d is advantageously located on the distal portion 60 of the main shaft 46, and may overlap into the intersection 55a thereof with the eyelet portion 48a. Where actuator 16a is used, the area of catheter hub 12 at 62 may be provided with a radially outwardly extending notch (not shown) sized with a cross dimension which may be smaller than that of the annular rib 65d so as to form a tight fit therebetween. Alternatively, the notch may be sized with a cross dimension slightly larger than that of the annular rib 65d such that the rib 65d may be positioned within the notch more easily, but yet still effectively secure the actuator 16a to the catheter hub 12.

The actuators 16, 16a may be formed from suitable materials including various metals and plastics and may be formed as a unitary or monolithic member. In alternative embodiments, however, the actuators 16, 16a may be formed from separate members which are subsequently coupled, such as through a welding or bonding process, to form the actuator. In an exemplary embodiment, the actuators 16, 16a may be formed from medical grade stainless steels (e.g., 410 stainless steel, 17-7 stainless steel, etc.) through processes generally known in the art.

Figure 5:
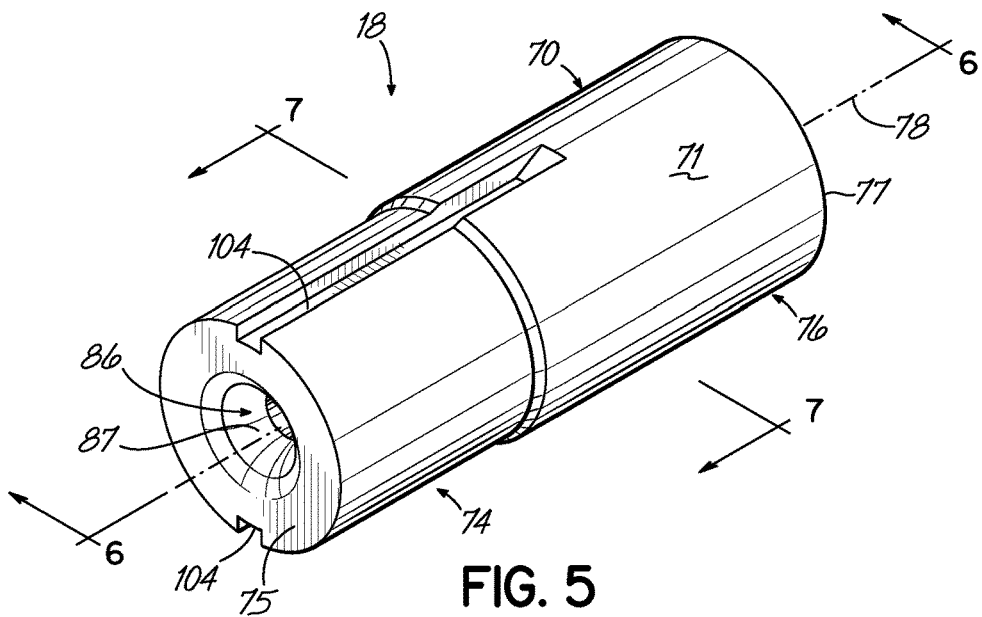
FIG. 5 is a perspective view of the seal member of FIGS. 1 and 2.
Figure 6:
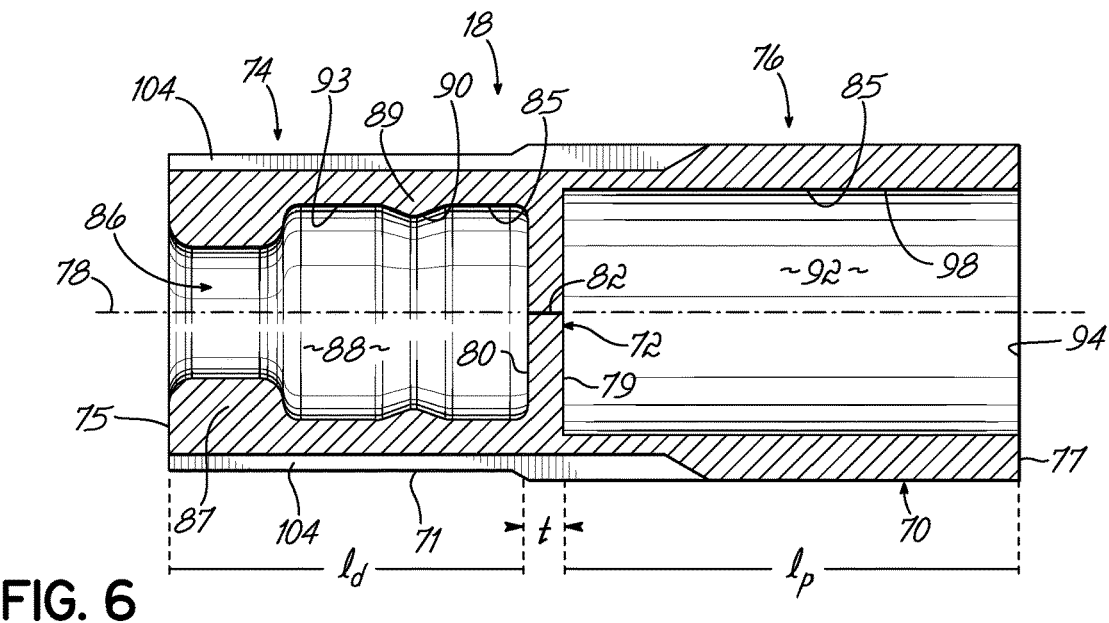
FIG. 6 is a cross-sectional view of the seal member shown in FIG. 5 taken generally along line 6-6 of FIG. 5.
Figure 7:
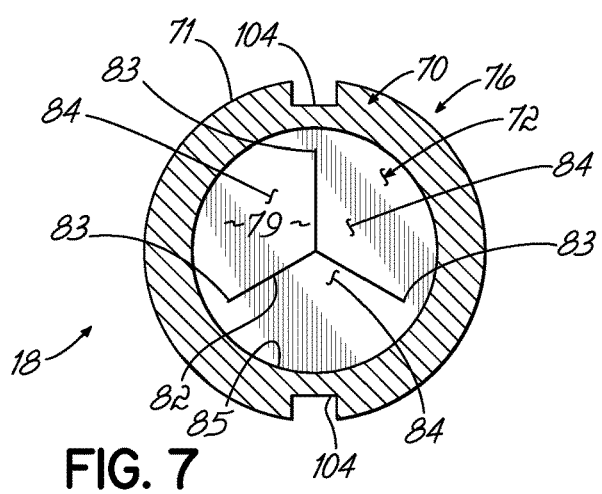
FIG. 7 is a cross-sectional view of the seal member shown in FIG. 5 taken generally along line 7-7 of FIG. 5.

As seen in FIG. 1, the seal member 18 is disposed within the interior cavity 24 of the catheter hub 12 and is supported therein at least in part by the actuator 16. The seal member 18 may also be supported in part by the inner wall 25 of catheter hub 12, as will be explained below. With further reference to FIGS. 5 through 7, the seal member 18 includes a generally cylindrical body 70 with an outer surface 71 and a central membrane 72, a distal portion 74 extending distally from the membrane 72 and terminating in a distal end 75, and a proximal portion 76 extending proximally from the membrane 72 and terminating in a proximal or impact end 77. The membrane 72 extends substantially perpendicularly relative to a central axis 78 and along a plane centrally located between proximal and distal ends 77, 75 of the seal member 18. In one embodiment, the membrane 72 has a generally constant axial thickness having generally planar upper and lower surfaces 79, 80, respectively, and includes a normally-closed slit 82 that extends completely through the axial thickness of the membrane 72. In an alternative embodiment, the upper and lower surfaces 79, 80 of membrane 72 may not be planar, but may have other configurations including, for example, concave or convex configurations.

The slit 82 may take several forms recognized in the art and could, for example, be a single straight slit (not shown) through the membrane 72. Advantageously, and in the embodiment shown herein, the slit 82 has a tri-slit configuration that extends to three radially outermost ends 83 to present a Y-shape when viewed in plan view as shown in FIG. 7. The slit 82 defines a plurality of membrane flaps 84, the number of which depends on the particular configuration of the slit 82 (e.g., three flaps 84 for a tri-slit configuration). Additionally, the length of the slit 82 (e.g., its radial extent) is preferably less than a cross dimension (e.g., diameter) of the membrane 72 such that the radially outermost ends 83 of the slit 82 are spaced from, and the slit 82 does not penetrate into, the inner surface 85 of the cylindrical body 70 of the seal member 18. In the ready position of the PIVC 38, the slit 82 in the membrane 72 and the needle shaft 41 may cooperate so as to form a substantially fluid tight seal about the needle shaft 41 when it extends through the membrane 72 (FIG. 2). However, the slit 82 and needle shaft 41 may not be fluid tight, but advantageously may still provide a significant restriction to blood flow through the membrane 72 when the needle shaft 41 extends therethrough, such that, for example, only a de minimus amount of blood may seep through the slit 82 of the membrane 72 during insertion of the catheter tube 14 into the vasculature of a patient (not shown).

The distal portion 74 of the seal member 18 includes a sealing outlet bore 86 defined by an annular sealing lip 87 extending proximally inward from the distal end 75, and an actuator cavity 88 between the sealing outlet bore 86 and the lower surface 80 of the membrane 72. The free end 51 of the actuator 16 is receivable through the sealing outlet bore 86 and into the actuator cavity 88 with the barb 50 contained in the actuator cavity 88 (FIG. 1). The actuator cavity 88 advantageously includes a narrowed portion 89 that provides the actuator cavity 88 with an hourglass shape (FIG. 6). For example, the narrowed portion 89 may be provided by an annular rib 90 projecting generally radially inward from the portion 93 of the inner wall 85 that defines the actuator cavity 88. In the closed position of the seal member 18 as shown in FIG. 1, frustoconical surface 57 of the actuator 16 engages with annular rib 90.

The proximal portion 76 of the seal member 18 is advantageously cylindrical and includes a generally cylindrical bore 92 extending between the membrane 72 and an opening 94 at the proximal end 77. The bore 92 may have a generally constant cross dimension along the length thereof. The opening 94 into, and advantageously the cylindrical bore 92, are configured such that neither the standard luer dimensioned nose, nor a standard dimensioned luer taper 30 (FIG. 9), can pass into the bore 92 but instead will, at most, impact against end 77. To that end, and as seen in FIG. 2, the nose 42 to be used with the catheter assembly 10 shown herein has a proximal aspect 42a defining a standard luer taper cross dimension so as to engage with wall 25 adjacent proximal end 20 of the catheter hub, and a reduced cross dimension distal aspect 95 with a uniform cross dimension along its length and sized to pass into the bore 92. However, the length of distal aspect 95 is selected so that the distal end 96 thereof does not unduly press against upper surface 79 of the membrane 72 in the ready position so as to avoid deformation of the membrane 72 which might adversely affect any seal between the slit 82 and the shaft 41 of the needle cannula 40. A recessed bore 97 may be formed in the distal end 96 for purposes to be described.

The normal length of a nose that would extend into the luer tapered proximal section 26 of the catheter hub 12 is expected to provide a reasonably reliably frictional engagement therebetween such that the nose does not fall out of the catheter hub 12, but can be easily removed therefrom with a slight force by the clinician (not shown). Due to the reduced cross dimension distal aspect 95, there is not as much engagement between the nose proximal aspect 42a and the inner wall 25 of the catheter hub 12. To avoid an unduly loose fit that might otherwise obtain, the distal aspect 95 may advantageously be sized to frictionally engage within the bore 92. Alternatively or additionally, a radially inwardly directed rib or projection(s) (not shown) may be formed on portion 98 of the inner wall 85 of the bore 92 to more securely engage with the distal aspect 95 of the nose 42.

The membrane 72 that closes the seal member 18 is located intermediate the proximal and distal ends 77, 75 of the seal member 18 (i.e., not at one of its ends). In this regard, the seal member 18 may be characterized by the membrane 72 having an axial thickness t that is substantially less than each of the axial length $l_p$ of the proximal portion 76 and the axial length $l_d$ of the distal portion 74. By way of example and without limitation, the axial lengths $l_p$ and $l_d$ may range between 7 to 15 times thickness t. In an exemplary embodiment, the thickness t of the membrane 72 may be about 0.015 to about 0.020 inches, while the lengths $l_p$ and $l_d$ may be approximately 0.235 inches and about 0.155 to about 0.16 inches, respectively.

As shown in FIG. 1, in the closed position of the seal member 18, the actuator 16 extends through the sealing outlet bore 86 such that the barb 50 is disposed within the actuator cavity 88. More particularly, the sealing lip 87 of the sealing outlet bore 86 is in sealing engagement with the outer surface 47 of the actuator main shaft 46 so as to substantially seal the actuator cavity 88 from below. The main shaft 46 of the actuator 16 is advantageously sized in cross dimension to receive the largest diameter needle cannula that might be employed with catheter assembly 10, with the eyelet portion 48 or 48a thereof sized to conform more closely to the specific needle cannula 40. As a consequence, the sealing outlet bore 86 can be a common size across the spectrum of needle cannula such that the same seal member 18 can be used across the range of expected needle cannula gauges, rather than necessarily requiring a different seal member 18 for each gauge, or a group of gauges.

Additionally, the barb 50 is completely contained in the actuator cavity 88 and may be in engagement with the narrowed portion 89 as explained earlier. The barb 50 has an outermost cross dimension larger than a cross dimension of the sealing outlet bore 86 and is configured to allow the sealing outlet bore 86 to be slid distally over the barb 50, but restricts proximal movement of the seal member 18 back over the barb 50.

In the closed position, the seal member 18 is completely disposed within the interior cavity 24 of the catheter hub 12 so as to be spaced from both the proximal and distal ends 20, 22 thereof. To that end, the proximal end 77 of the seal member 18 is spaced from the opening 21 at the proximal end 20 of the catheter hub 12 by a distance $d_p$ so as to define a space P1 proximal of the seal member 18, and the distal end 75 of the seal member 18 is spaced from the distal cavity 28 of the catheter hub 12 by a distance $d_d$ so as to define a space D1 distal of the seal member 18. In an exemplary embodiment, $d_p$ may be about 0.045 inches and $d_d$ may be between about 0.085 and about 0.17 inches. Additionally, the membrane 72 is positioned proximally of the free end 51 of the actuator 16 such that the normally-closed slit 82 formed therein substantially seals the actuator cavity 88 from above. Accordingly, and as will be explained in more detail below, should blood flow into actuator cavity 88 of the seal member 18 during insertion of the catheter assembly 10, for example, the actuator cavity 88 is substantially fluidly isolated (e.g., sealed) from below by the sealing lip 87/actuator wall 47 engagement and above by the normally-closed slit 82 of the membrane 72 such that substantially no blood can flow therebeyond and into the interior cavity 24 of the catheter hub 12.

In some previously proposed designs, an elongated member extends into the catheter hub and the seal is pushed thereagainst to open same. But the seal in those proposed designs has typically either been freely floating on the elongated member so as to be spaced along its entire circumference from the catheter hub wall, or the seal is in full circumferential engagement with the wall of the catheter hub. Each approach is considered to present disadvantages. Free floating seals may lack sufficient support within the catheter hub and may be subject to undue sideways or similar movement or tilting. Seals that are in full circumferential engagement with the catheter hub wall may suffer from relatively large friction forces at the seal/catheter hub wall interface, and may therefore require a relatively large force to move the seal to the opened position during actuation. These types of seals may have other shortcomings as well. For example, due to the full circumferential engagement, pressure build ups are possible when the seal is actuated because air, for example, cannot escape the space distally of the seal as it is being moved axially within the catheter hub into that space. Such pressure build ups are undesirable and may require unduly large actuation forces to operate.

In accordance with another feature of the present invention, seal member 18 is supported by both the actuator 16 and the catheter hub 12, but in the closed position, the outer surface 71 is only in partial circumferential engagement with the inner wall 25 of the catheter hub 12 along an outer contacting region 100 thereof (FIG. 1) so as to maintain at least one air path 102 (as exemplified by arrows 102 in FIG. 1) between the spaces P1 and D1 proximal and distal, respectively, of the seal member 18. Advantageously, two such air paths 102 are provided. To that end, at least along the contacting region 100 of the seal member 18, the outer surface 71 of the seal member 18 may include at least one axially-directed channel or groove 104 extending inwardly from the outer surface 71 and which defines a portion, if not the entirety, of the air path 102 therealong. Where two or more axial grooves 104 are provided, each defines a portion, or the entirety, of a respective air path 102. Advantageously, only a short axial portion of the outer surface 71 is engaged in contacting region 100, such that the areas proximal and distal thereof are spaced away from the inner wall 25 of the interior cavity 24 as at 105 and 106 as illustrated for example in FIG. 1. The areas 105 and 106 also define a portion of the air path(s) 102, and have the further advantage of reducing friction between the seal member 18 and the catheter hub 12 so that the seal member 18 is more readily slidable within the catheter hub 12 to open same as will be described below. Provision of the air path(s) 102 allows the outer surface 71 of the seal member 18 to be in circumferential engagement with the inner wall 25 of the catheter hub 18 in the engagement area 100, except in the area of the axial groove(s) 104 so as to define a partial circumferential engagement. As a consequence, the seal member 18 is held in a stable position on the actuator 16, but also facilitates fluid communication between areas P1 and D1 of the interior cavity 24 proximal and distal of the seal member 18 so as to prevent excessive pressure build up during actuation of the seal member 18 and to reduce the surface area contact between the seal member 18 and the inner wall 25 of the catheter hub 12 thereat to thus minimize frictional forces imposed on the seal member 18 during actuation.

The distal area 106 may be achieved by reducing the outer cross dimension of the seal member 18 along the distal portion 74 thereof and/or increasing the cross dimension of the second section 31 of the interior cavity 24 adjacent the distal portion 74 of the seal member 18. Similarly, the proximal area 105 may be achieved by reducing the outer cross dimension of the seal member 18 along the proximal portion 76 thereof and/or increasing the cross dimension of the first section 29 of the interior cavity 24 of the sealing member adjacent the proximal portion 76 of the sealing member 18. For example, the proximal area 105 may be a result of the luer tapering of the first section 29 of the proximal portion 26 of the interior cavity 24 while maintaining the outer cross dimension of the proximal portion 76 of the seal member 18 relatively constant, as shown in FIG. 1.

The contacting region 100 between the seal member 18 and catheter hub 12 may occur along the membrane 72 and the distal-most portion of the proximal portion 76 of the sealing member 18. Notably, however, the axial groove(s) 104 extend at least from a location distal of the contacting region 100 to a location proximal of the contacting region 100. Accordingly, depending on the particular size of the contacting region 100, the axial groove(s) 104 may extend the full length of the seal member 18 or for only a portion thereof (so long as they extend axially sufficiently to define any portion of the associated air path 102 through the engagement area 100, whether they extend therebeyond is not controlling, but may be advantageous). In one embodiment, each axial groove 104 is open to the distal end 75 of the seal member 18, but stops short of extending to the proximal end 77 thereof (FIG. 6). Moreover, the depth of the axial groove(s) 104 is such as to not penetrate through the inner surface 85 of the seal member 18 in either the sealing outlet bore 86 or the actuator cavity 88, as well as, advantageously, in bore 92.

With further regard to FIG. 2, the cap 44 is sized such that it does not fit within the proximal opening 20 of the catheter hub 12. Instead, the cap 44 may abut a proximal end face 110 of the catheter hub 12 when the PIVC 38 is in the ready position. The cap 44 may also include a continuous or segmented collar or rim (not shown) adapted to fit over, and possibly releaseably engage, external luer lock receiving ears 112 of the catheter hub 12 defined adjacent end face 110. A step (not shown) may be defined at a distal aspect of the receiving ears 112 that may facilitate assembly of the catheter assembly 10. Advantageously, in the ready position, the cap 44 is against end face 110 and the nose 42 extends into the interior cavity 24 with proximal aspect 42a thereof fitting snugly against the inner wall 25 of the catheter hub 12. The distal segment 95 is sized so as to fit within the bore 92 such that the distal end 96 is adjacent or engaging the upper surface 79 of membrane 72. In the event the distal end 96 contacts the membrane 72, it does not penetrate through the slit 82 thereof. Additionally, the bore 97 at the distal end 96 is positioned so as to overlie the slit 82 in the membrane 72.

In use, and from the ready position as illustrated in FIG. 2, the sharp tip 43 of PIVC 38 is inserted into the artery or vein of the patient (not shown) in the conventional manner. The needle shaft 41 may include a slot 114 therethrough adjacent the sharp tip 43 to provide blood flashback. The use of the slot 114 in the needle cannula 40 may be partially advantageous for large gauge needle cannula 40 (i.e., smaller diameter needle cannula 40). In addition to, or in lieu of, the cannula slot 114, the needle cannula 40 may couple to a flash chamber (not shown) adjacent the proximal end (not shown) of the needle cannula 40 for blood flashback as is conventional.

After insertion of the catheter tube 14 into the patient, the needle cannula 40 is withdrawn proximally from the catheter tube 14 and the catheter hub 12 while leaving the catheter assembly 10 in fluid communication with the vasculature of the patient. As the needle cannula 40 is being withdrawn, the drag force imposed on the seal member 18 (e.g., on the slit 82 of the membrane 72) due to the proximal movement of the needle cannula 40 is insufficient to overcome the forces retaining the seal member 18 in the catheter hub 12. Accordingly, the seal member 18 remains positioned within the catheter hub 12 during proximal withdrawal of the needle cannula 40. More particularly, the force imposed by the sealing lip 87 on the actuator 16 (which is fixedly secured to the catheter hub 12 as previously described), the friction force of the seal member 18 engaging the inner wall 25 of the catheter hub 12 along contacting region 100, as well as any friction forces generated between the barb 50 and the inner wall 85 of the actuator cavity 88 may individually or collectively resist proximal movement of the seal member 18 relative to the catheter hub 12 upon withdrawing the needle cannula 40. Even if there should be some initial proximal movement of the seal member 18 relative to the catheter hub 12, the barb 50 of actuator 16 is larger than the sealing outlet bore 86 of seal member 18 such that any initial axial movement of the seal member 18 would be arrested.

Figure 8:
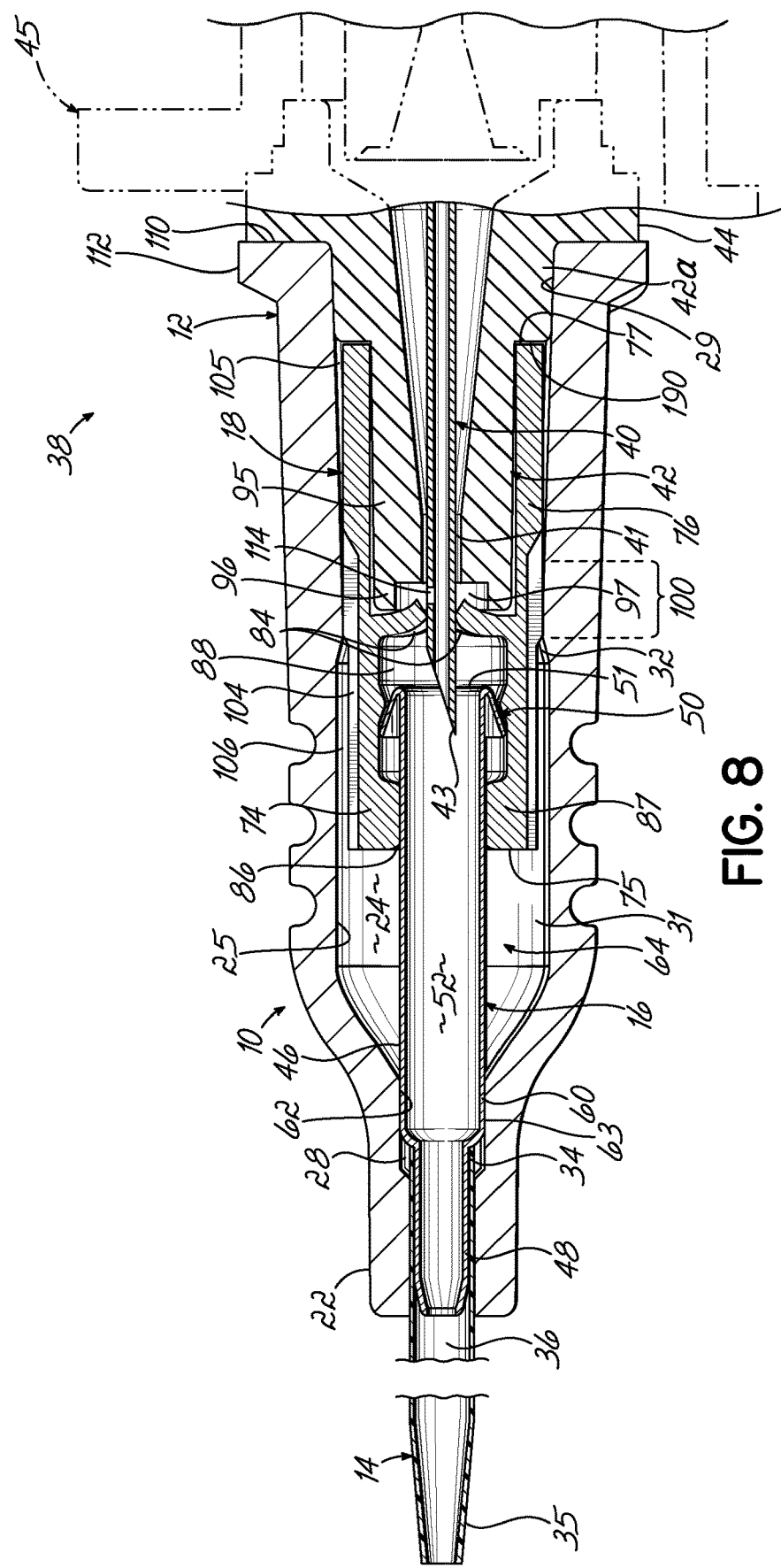
FIG. 8 is a view similar to FIG. 2, but showing the needle cannula being withdrawn proximally for explaining a feature of the present invention.

Furthermore, during proximal withdrawal of the needle cannula 40, the drag force acting on the slit 82 of the membrane 72 may cause one or more of the flaps 84 formed by the slit 82 to slightly flex or distend upwardly (i.e., proximally). More particularly, the slot 114 may engage with one of the flaps 84 as it passes proximally through the slit 82 to flex or distend the flap 84. The nose 42 remains within the catheter hub 12 during such withdrawal, such that the upward flexing of the flaps 84 is into the recessed bore 97 as shown in FIG. 8, rather than against the distal end 96 of the nose 42, thereby reducing the risk of damage to the flaps 84 and the negative affect that might have on the sealing capability of the slit 82. Where the nose 42 and the needle cannula 40 are secured such that the nose 42 moves with proximal movement of the needle cannula 40, the recessed bore 97 may be omitted.

In addition to the above, the drag force on the seal member 18 generated by withdrawing the nose 42 from the catheter hub 12 is also insufficient to overcome the forces retaining the seal member 18 in the catheter hub 12. Thus, for example, the slip fit between the reduced cross section distal aspect 95 of the nose 42 and the bore 92 of the seal member proximal portion 76 is not so tight as to cause the seal member 18 to be pulled out of the catheter hub 12 during proximal withdrawal of the nose 42 from the catheter hub 12. Similar to above, even if there should be some initial proximal movement of the seal member 18 relative to the catheter hub 12, the barb 50 of the actuator 16 is larger than the sealing outlet bore 86 of the seal member 18 such that any initial proximal movement of the seal member 18 would be arrested.

After the needle cannula 40 has been withdrawn and the nose 42 separated from the catheter assembly 10, the seal member 18 within the catheter hub 12 is in the closed or sealed position to prevent blood from the patient from flowing into the interior cavity 24 of the catheter hub 12 (FIG. 1). More particularly, during and after insertion of the catheter tube 14 into the patient's vasculature (e.g., during proximal withdrawal of the needle cannula 40, or after the needle cannula 40, and possibly the nose 42, have been proximally withdrawn from the catheter hub 12), blood from the patient may flow up through the catheter tube 14, through the actuator 16, and into the actuator cavity 88 of the seal member 18, in which the proximal free end 51 of the actuator 16 is disposed. In other words, an unobstructed fluid flow path exists between the distal end 35 of the catheter tube 14 and the proximal free end 51 of the actuator 16 such that blood may flow therebetween. Advantageously, however, blood that flows into the actuator cavity 88 is substantially prevented from flowing out of the cavity 88 such that hemostasis is achieved or maintained.

To this end, the sealing lip 87 of the outlet bore 86 forms a substantially fluid tight seal with the outer surface 47 of the actuator main shaft 46 to prevent any blood flow out of actuator cavity 88 along this interface (e.g., the actuator cavity 88 is effectively sealed from below). Additionally, after the needle cannula 40 has been removed from the membrane 72, the slit 82 closes due to the resiliency of the material that forms the membrane 72 (i.e., the slit 82 is normally closed). The closing of the slit 82 substantially prevents blood flow out of the actuator cavity 88 through the membrane 72. Advantageously, the slit 82 is sufficiently closed so that essentially no blood seeps through the slit 82 and past the membrane 72 under the pressures normally observed during use.

As noted above, even if there should be some seepage through the slit 82 of the membrane 72, the amount of blood would be de minimus and hemostasis during and after insertion of the catheter tube 14 (but prior to actuation of seal member 18) would still be sufficiently maintained. Accordingly, should blood flow into actuator cavity 88 of the seal member 18, the cavity 88 is substantially fluidly isolated (e.g., sealed) from below by the sealing lip 87/actuator surface 47 engagement and above by the closed slit 82 of the membrane 72 such that substantially no blood can flow therebeyond. This allows medical personnel to address other pressing issues without worry that blood is going to flow out of the catheter hub 12 in the interim.

The seal member 18 is configured to not only provide blood control during use, but the seal member 18 is further configured to be actuated so as to open a fluid flow path from the catheter tube 14. Advantageously, and as illustrated in FIGS. 9 and 10, the seal member 18 may be configured such that it is axially shiftable so as to slide axially along the main shaft 46 of the actuator 16, to the opened position. That shifting is accomplished by insertion of a male luer taper 30 into and through the proximal end 20 of the catheter hub 12 such that the free or distal end 120 thereof impacts surface proximal end 77 of the seal member 18 and pushes the seal member 18 distally with enough force to overcome the friction forces holding the seal member 18 in place. To that end, the luer taper 30 may be associated with a luer lock collar or nut 122 adapted to threadably engage catheter hub ears 112 so as to impel the luer taper 30 against proximal end 77. That causes the luer taper 30 to push thereagainst over a travel distance which axially shifts the seal member 18 driving the membrane 72 over the actuator barb 50 and distending the flaps 84 placing the seal member in the opened condition. The catheter assembly 10 is configured such that the entire seal member 18 axially shifts distally within the catheter hub 12.

As the seal member 18 axially shifts within the catheter hub 12, the proximal free end 51 of the actuator 16 contacts the lower surface 80 of the membrane 72 and starts penetrating through the slit 82 causing the flaps 84 formed by the slit 82 to hinge or distend upwardly and slide along the barb 50, such as along the frustoconical surface 57 thereof, so as to gradually open the slit 82. Continued distal insertion of the luer taper 30 causes the seal member 18 to shift axially until the luer taper 30 is fully extended into the interior cavity 24 with the distal end 75 of the seal member 18 moved toward, or against, distal cavity 28 to thus define the open position of the seal member 18 as shown in FIG. 10. In one embodiment, the membrane 72 is sufficiently resilient such that the barb 50 may penetrate the slit 82 without ripping or otherwise destroying the membrane 72. The slit 82 may then close back down around the actuator main shaft 46 after the barb 50 passes therethrough. In an alternative embodiment, the membrane 72 may be deformed, or may be ripped or otherwise destroyed, as the barb 50 penetrates through the slit 82. This is illustrated, for example, by the broken appearance of the membrane 72 in FIG. 10.

In the opened position of the seal member 18, an unobstructed fluid path is established between the catheter tube 14 and the luer taper 30 via the actuator 16 such as for administration of fluids to, or withdrawal of blood from, the patient with the catheter assembly 10. Advantageously, the seal member 18 and the catheter hub 12 are sized such that in the opened position, the seal member 18 is not under axial compression, i.e., the seal member 18 is not being axially squeezed between the luer taper 30 and the distal end 22 of the catheter hub 12. In this regard, the travel distance $d_t$ of the seal member 18 between the closed and opened position is configured to be less than the distance $d_d$ between the distal end 75 of the seal member 18 and the distal cavity 28 of the catheter hub 12. In an exemplary embodiment where $d_d$ is about 0.17 inches, the travel distance $d_t$ may be approximately 0.163 inches. The invention, however, is not so limited as in an alternative embodiment, there may be some axial compression on the seal member 18 when in the opened position.

In the embodiment shown and described herein, the seal member 18 is a one-time use seal. In this regard, after removal of the luer taper 30 from the catheter hub 12, the seal member 18 will not move back proximally to the closed position, but will instead remain in the opened position. More particularly, the barb 50, while configured to permit movement of the seal member 18 in the distal direction, discourages movement of the seal member 18 in the opposite, proximal direction. Thus, the membrane 72 in the embodiment shown does not automatically move back over the barb 50 to close off the fluid flow path established with the catheter tube 14 which instead now provides an unobstructed fluid flow path between the catheter tube 14 and interior cavity 24 and/or the open proximal end 20 of the catheter hub 12. In another embodiment, however, the catheter assembly could be provided with a mechanism, such as a spring, elastic, or bellows, to provide a driving force axially shifting the seal member 18 back in the proximal direction to reclose the seal member 18. Exemplary embodiments of such a multi-use seal are discussed in more detail below. However, in the embodiment shown in FIGS. 1, 2 and 5-10, the seal member 18 is a one-time use seal for providing hemostasis and once it is opened, it is not intended to be re-closed.

Figures 11, 12:
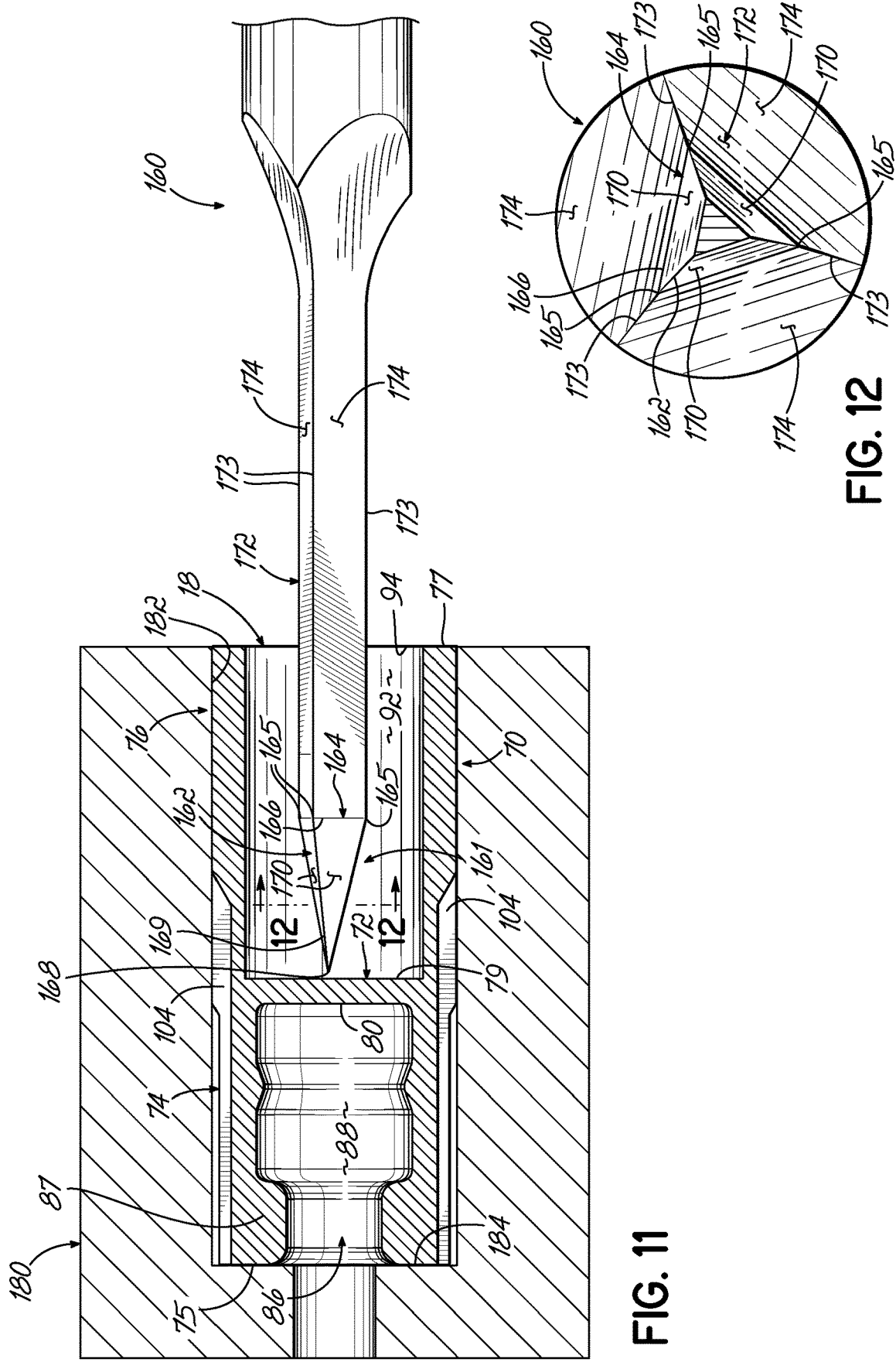
FIG. 11 is a view showing the seal member of FIG. 1 and a fixture in cross section, and a punch tool for use therewith for forming a tri-slit in the membrane of the seal member.
FIG. 12 is a cross-sectional view of the end of the punch tool shown in FIG. 11 taken generally along line 12-12 of FIG. 11.

The seal member 18 may be generally flexible and be formed from suitable materials including, for example, silicone or polyisoprene. In one embodiment, the seal member 18 may be formed as a unitary or monolithic member through various molding processes including, for example, injection molding processes generally known in the art. The slit 82 is generally not molded into membrane 72, but is instead formed in a post-molding process. In this regard, and as illustrated in FIGS. 11 and 12, a punch or slit tool 160 may be used to form the tri-slit 82 in the membrane 72. Conventional tools for creating a tri-slit (not shown) generally include a flat-headed punch having a shape corresponding to the shape of the tri-slit. Such tools, however, when used on resilient materials often stretch the material during the punching operation such that sufficient support must be provided directly beneath the material being slit to prevent tearing or causing other damage.

To overcome such a drawback, the slit tool 160 includes a distal end 161 formed by a three-sided pyramid 162 having a base 164 with three corners 165 at one end 166 thereof, and terminating in a pointed tip 168 at the other end 169 thereof so as to define three diverging surfaces 170 of the pyramid 162. The tool 160 further includes a shaft 172 having generally straight, sharpened edges 173 with generally planar lands 174 therebetween. The pyramid 162 is coupled to the shaft 172 such that the edges 173 generally axially align with the respective corners 165 of the base 164. As shown in FIG. 12, to form the tri-slit 82, the molded seal member 18 may be placed in a fixture 180 having a bore 182 sized to receive the seal member 18 therein. The bore 182 includes a bottom wall 184 configured to engage the distal end 75 of the seal member 18 within the fixture 180. The tool 160 is inserted through the proximal opening 94 of the bore 92 in the seal member 18 so as to engage the pointed tip 168 against the upper surface 79 of the membrane 72. Insertion of the tool 160 is continued such that the pointed tip 168 and the diverging surfaces 170 ease, at least partially, through the seal member 18 so as to gradually increase the length of the slit 82 until the desired tri-slit configuration is achieved.

It should be realized that in an alternative embodiment, as shown in FIGS. 11A and 11B, the seal member 18 may be inverted within fixture 180 such that the proximal end 77 of the seal member 18 engages the bottom wall 184 and the tool 160 is inserted through the sealing outlet bore 86 and actuator cavity 88 so as to engage against the lower surface 80 of the membrane 72. When forming the slit 82 with the seal member 18 in this orientation, a spreader tool 186 may be provided for increasing the size of the sealing outlet bore 86 so as to allow passage of the slit tool 160 therethrough without contacting or otherwise damaging the seal member 18. In this regard, the spreader tool 186 includes an annular flange 188 and three tabs 190 extending distally therefrom and arranged in a generally triangular configuration that generally corresponds to the three sides of the pyramid 162 and shaft 172 of slit tool 186. An outer surface 192 of the tabs 190 is contoured to define a thin-walled portion 194 at the distal tip of the tabs 190 and a thick-walled portion 196 proximal of the thin-walled portion 194 and into which the thin-walled portion 194 smoothly transitions (e.g., a taper). The tabs 190 are dimensioned such that the thin-walled portion 104 of the tabs 190 fit within the confines of the sealing outlet bore 86. However, as shown in FIG. 11B, as the spreader tool 186 is moved toward the fixture 180, the contoured shape of the outer surface 192 of the tabs 190 causes the sealing outlet bore 86 to stretch outwardly about the triangular configuration of the tabs 190 thereby increasing the size of the sealing outlet bore 86. The fixture 180 may include an annular cutout 198 to accommodate the outward speading of the seal member 18 as the spreader tool 186 is inserted therein. The distal movement of the spreader tool 186 toward the fixture 180 may be stopped by engagement of the flange 188 with the proximal end 199 of the fixture 180. With the spreader tool 186 inserted so as to increase the size of the sealing outlet bore 86, the slit tool 160 may pass through the spreader tool 186 and sealing outlet bore 86 so as to form the slit 82 in membrane 72 without contacting or otherwise damaging the seal member 18.

It should be realized that in either orientation of the seal member 18 within fixture 180, the membrane 72 need not be directly supported, although a support (not shown) may be provided beneath the membrane 72 if desired. The configuration of the tool 160 provides for a clean slit 82 and reduces the likelihood of damaging the seal member 18 during the slit-forming process.

The catheter assembly 10 may be assembled as follows. The actuator 16 may be inserted through the proximal opening 21 of the catheter hub 12 such that the distal eyelet portion 48 or 48a captures the proximal end 34 of the catheter tube 14 within the distal cavity 28 of the catheter hub 12. Alternatively, the proximal end 34 of the catheter tube 16 may be coupled to eyelet portion 48, 48a of the actuator 16, 16a and that subassembly inserted through the proximal opening 21 of the catheter hub 12 so as to capture the proximal end 34 of the catheter tube 16 within the distal cavity 28. In either embodiment, the actuator 16, 16a will be situated to project proximally from the distal end 22 of the catheter hub 12 within the interior cavity 24. The seal member 18, which may be formed by the method described above, is threaded onto the needle cannula 40. In one embodiment, the sharp tip 43 thereof may simply be inserted through the slit 82 in membrane 72 and the seal member 18 threaded onto the needle shaft 41. In an alternative embodiment, the needle cannula 40 may be extended through the membrane 72 in a manner that reduces potential damage to the membrane 72. To this end, a small tube (not shown) may first be inserted through the slit 82. The small tube is configured to be generally smooth (e.g., devoid of any sharp edges, burrs, etc.) and relatively soft and may be formed of a suitable plastic material. After positioning the tube through the slit 82, the needle cannula 40 may then be inserted through the tube such that the sharp tip 43 cannot directly engage the membrane 72 as the needle cannula 40 is extended through the slit 82. Thereafter, the tube is pulled out of the slit 82 and over the needle cannula 40, such as over the sharp tip 43 thereof, allowing the slit 82 and needle shaft 41 to engage. In this way, the tube acts as a barrier between the membrane 72 and the needle cannula 40 during inserting of the needle cannula 40 through the slit 82 so as to avoid or reduce the likelihood of damage during assembly.

Once threaded onto needle shaft 40, the seal member 18 may be slidably positioned on the nose 42 with the distal aspect received in the bore 92 in proximal portion 76 of the seal member 18 in a slip fit, which may range from being relatively snug to providing just enough engagement to frictionally retain the seal member 18 on the nose 42. The distal aspect 95 of the nose 42 may be inserted into the bore 92 until the proximal end 77 of the seal member 18 abuts the annular shoulder 190 at the intersection of the nose aspects 42a and 95. When this occurs, the distal aspect 95 of the nose 42 may engage, or be slightly spaced from, the upper surface 79 of the membrane 72. In an alternative embodiment, the distal aspect 95 may be inserted into bore 92 until the distal end 96 thereof abuts the upper surface 79 of the membrane 72. When this occurs, the proximal end 77 of the seal member 18 may be slightly spaced from the annular shoulder 190. It will be readily understood that the needle cannula 40 may be retracted and the seal member 18 placed on the nose 42 prior to threading the needle cannula 40 to the seal member 18 as described above.

After the seal member 18 is disposed on the nose 42 and the needle cannula 40 extends distally thereof, the catheter assembly 10 may be loaded onto the nose 42 such that the seal member 18 is positioned within the catheter hub 12. In this regard, as the catheter assembly 10 and nose 42 are moved together, the sealing outlet bore 86 contacts the barb 50 and sealing lip 87 flexes outwardly (e.g., due to camming engagement of the sealing lip 87 and the frustoconical surface 57 of the flange 56) to allow the barb 50 to pass through the sealing outlet bore 86 and into the actuator cavity 88. When the sealing outlet bore 86 moves past the barb 50, the sealing lip 87 flexes or snaps back radially inwardly due to the resiliency of the seal member 18 and engages the outer surface 47 of the actuator 16 distal of the barb 50 to form a substantially fluid tight seal therealong.

The catheter assembly 10 and nose 42 may be moved further together until the cap 44 abuts the proximal end face 110 of the catheter hub 12. During this further movement, the sealing lip 87 of the sealing outlet bore 86 slides along the outer surface 47 of the actuator 16 and maintains the substantially fluid tight seal therealong. When the cap 44 and the catheter hub 12 engage, the seal member 18 is configured to be properly seated on the actuator 16 within the catheter hub 12 in the ready position. In this ready position, the barb 50 may engage the narrowed portion 89 of the actuator cavity 88 to provide a level of resistance to further distal movement of the seal member 18 relative to the actuator 16. During assembly, this resistance may also provide a positive indication that the seal member 18 is fully seated on the actuator 16.

Figure 13:
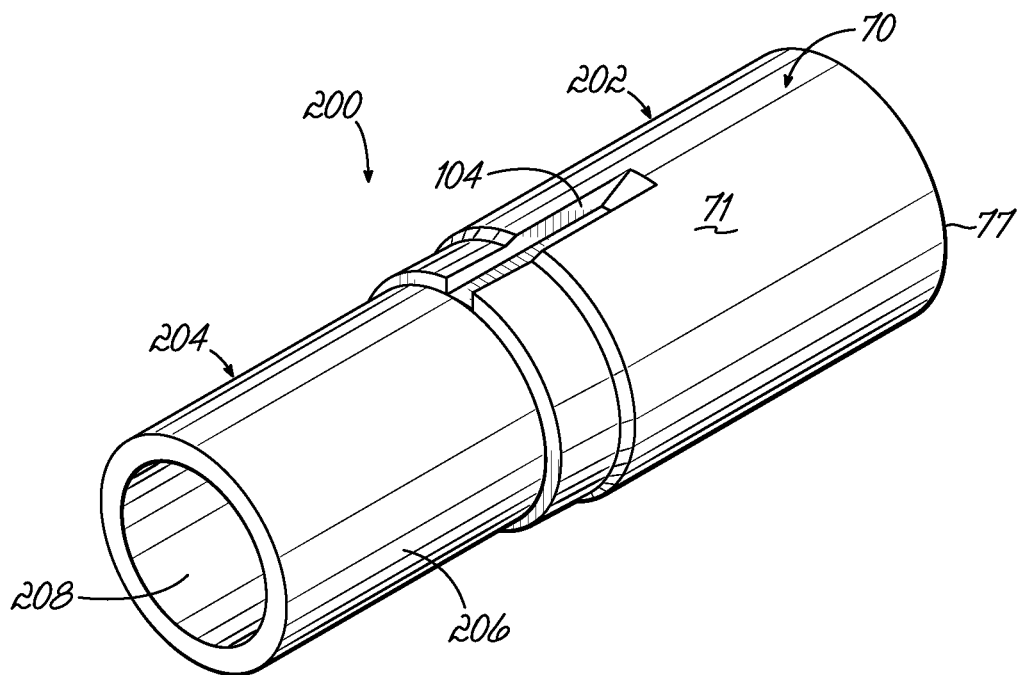
FIG. 13 is a perspective view of a multi-use seal member in accordance with a further feature of the present invention.

As noted above, in an alternative embodiment, the seal member of the catheter assembly may be configured as a multi-use seal, as opposed to a one-time use seal, wherein a driving force is provided to axially shift the seal member back in the proximal direction to reclose the seal member and re-establish hemostasis when the male luer taper is removed from the catheter hub. In this regard, FIG. 13, in which like reference numerals refer to like features in FIGS. 1-12, illustrates an exemplary multi-use seal member 200. The seal member 200 includes a proximal portion 202 that is substantially similar to the seal member 18 shown in FIGS. 5-7 and described in detail above. By way of example, proximal portion 202 may include the details of seal member 18 but be scaled down or shortened in a length direction (i.e., proximal-distal direction) so that the mechanism that provides the return driving force also fits within the catheter hub. Accordingly, the details of proximal portion 202 will not be further described. Unlike the previous embodiment, however, seal member 200 includes a biasing member 204 extending distally from proximal portion 202. In the illustrated embodiment, the biasing member 204 may include a generally thin-walled, circumferentially continuous tubular extension member 206 defining an open passageway 208 and integrally formed with proximal portion 202 so that seal member 200 forms a unitary member. Similar to the previous embodiment, the seal member 200 may be generally flexible and be formed from suitable materials including, for example, silicone or polyisoprene. Additionally, the seal member 200 may be formed through various molding processes including, for example, injection molding processes generally known in the art.

As one of ordinary skill in the art will readily appreciate, in use, seal member 200 operates similar to seal member 18 described above and therefore, only the differences in operation will be discussed in any significant detail. In this regard, the primary difference is in the actuation of the seal member 200 by the male luer taper 30. As illustrated in FIGS. 14 and 15, the seal member 200 may be configured such that it is axially shiftable so as to slide axially along the main shaft 46 of the actuator 16 to the opened position. That shifting is accomplished by insertion of male luer taper 30 into and through the proximal end 20 of the catheter hub 12 such that the free or distal end 120 thereof impacts surface proximal end 77 of the seal member 200 and pushes the seal member 200 distally with enough force to overcome the friction forces holding the seal member 200 in place. Similar to the above, the male luer taper 30 may be associated with a luer lock collar or nut 122 adapted to threadably engage catheter hub ears 112 so as to impel the luer taper 30 against proximal end 77. That causes the luer taper 30 to push thereagainst over a travel distance which axially shifts the seal member 200 driving the membrane 72 over the actuator barb 50 and placing the seal member in the opened condition.

As the seal member 200 axially shifts within the catheter hub 12, the proximal free end 51 of the actuator 16 contacts the lower surface 80 of the membrane 72 and starts penetrating through the slit 82 causing the flaps 84 formed by the slit 82 to hinge or distend upwardly and slide along the barb 50, such as along the frustoconical surface 57 thereof, so as to gradually open the slit 82. Continued distal insertion of the luer taper 30 causes the seal member 200 to shift axially until the luer taper 30 is fully extended into the interior cavity 24 with the seal member 200 moved toward distal cavity 28 to thus define the opened position of the seal member 200 as shown in FIG. 15. In this embodiment, the membrane 72 is sufficiently resilient such that the barb 50 may penetrate the slit 82 without ripping or otherwise destroying the membrane 72. The slit 82 may then close back down around the actuator main shaft 46 after the barb 50 passes therethrough.

Prior to or as the seal member 200 is axially shifted within the catheter hub 12, a distal end 210 of the tubular extension member 206 contacts the inner wall 25 of the catheter hub 12 adjacent the distal cavity 28 so that the tubular extension member 206 starts buckling or compressing with further distal axial shifting of the seal member 200. When the seal member 200 is in the opened position, the tubular extension member 206 is in a compressed condition and is configured to generate a restoring force that biases the seal member 200 back in the proximal direction toward the closed position. In this regard, tubular extension member 206 operates similar to a coil spring in that compression of the tubular extension member 206 generates a restoring force in a direction opposite to the compression. However, such proximal axial shifting of the seal member 200 back toward the closed position is prevented by the presence of the luer taper 30 in the catheter hub 12. Similar to the previous embodiment, in the opened position of the seal member 200, an unobstructed fluid path is established between the catheter tube 14 and the luer taper 30 via the actuator 16 such as for administration of fluid to, or withdrawal of blood from, the patient with the catheter assembly.

In this embodiment, the seal member 200 is configured as a multi-use seal and is therefore configured to move from the opened position back to the closed position. In this regard, when the male luer taper 30 is removed from the catheter hub 12, the biasing force generated by the compression of the tubular extension member 206 causes the seal member 200 to axially shift in the proximal direction. To this end, the biasing force imposed by the tubular extension member 206 is sufficient to overcome the frictional forces between the seal member 200 and the actuator 16 and the seal member 200 and the inner wall 25 of the catheter hub 12. More particularly, as the seal member 200 moves proximally under the biasing force, the distal end 212 of barb 50 contacts the upper surface 79 of the membrane 72 causing the flaps 84 formed by slit 82 to hinge downwardly and thereby allow the barb 50 to pass back through the slit 82.

After the barb 50 has been removed from the membrane 72, the slit 82 closes due to the resiliency of the material that forms the membrane 72 (i.e., the slit 82 is normally closed). The closing of the slit 82 substantially prevents blood flow out of the actuator cavity 88 through the membrane 72. Advantageously, the slit 82 is sufficiently closed so that essentially no blood seeps through the slit 82 and past the membrane 72. As noted above, even if there should be some seepage through the slit 82 of the membrane 72, the amount of blood would be de minimus and hemostasis would be sufficiently re-established. Accordingly, should blood flow into actuator cavity 88 of the seal member 200, the cavity 88 is substantially fluidly isolated (e.g., sealed) from below by the sealing lip 87/actuator surface 47 engagement and above by the closed slit 82 of the membrane 72 such that substantially no blood can flow therebeyond. Of course the seal member 200 may be axially shifted back to the opened position in the manner described above. Due to biasing member 204, the seal member 200 is configured to be repeatedly moved between its opened and closed positions therefore providing the multi-use aspect of this design.

Figure 16:
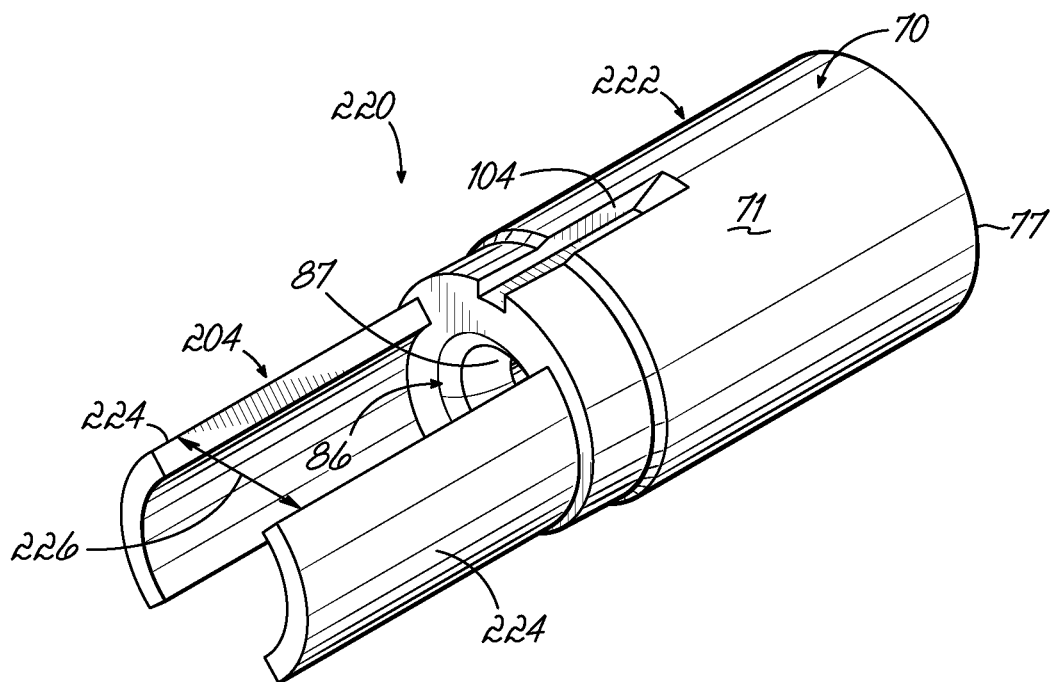
FIG. 16 is a perspective view of an alternative multi-use seal member.

FIG. 16 illustrates a multi-use seal member 220 in accordance with an alternative embodiment. Similar to seal member 200, seal member 220 includes a proximal portion 222 that is substantially similar to the seal member 18 shown in FIGS. 5-7 and described in detail above. Similarly, proximal portion 222 may include the details of seal member 18 but be scaled down or shortened in a length direction so that the mechanism that provides the return driving force also fits within the catheter hub. Accordingly, the details of proximal portion 222 will not be further described. Additionally, seal member 220 includes a biasing member 204 extending distally from proximal portion 222. In the illustrated embodiment, the biasing member 204 may include a pair of generally opposed, thin-walled legs 224 integrally formed with proximal portion 222 so that seal member 220 forms a unitary member. In one embodiment, for example, the legs 224 may be generally arcuate and take the form of constant radius tubular segments. While the illustrated embodiment shows two such legs 224, it should be realized that seal member 220 may include fewer or additional legs 224 that generate the driving force that axially shifts the seal member 220 back in the proximal direction to reclose the seal member 220. As one of ordinary skill in the art will readily understand the operation of a catheter assembly having seal member 220, its operation will not be described in further detail. It should be noted, however, that the spacing or gap 226 between the legs 224 cooperate with the grooves 104 to provide an air escape path during actuation of seal member 220.

Figure 17:
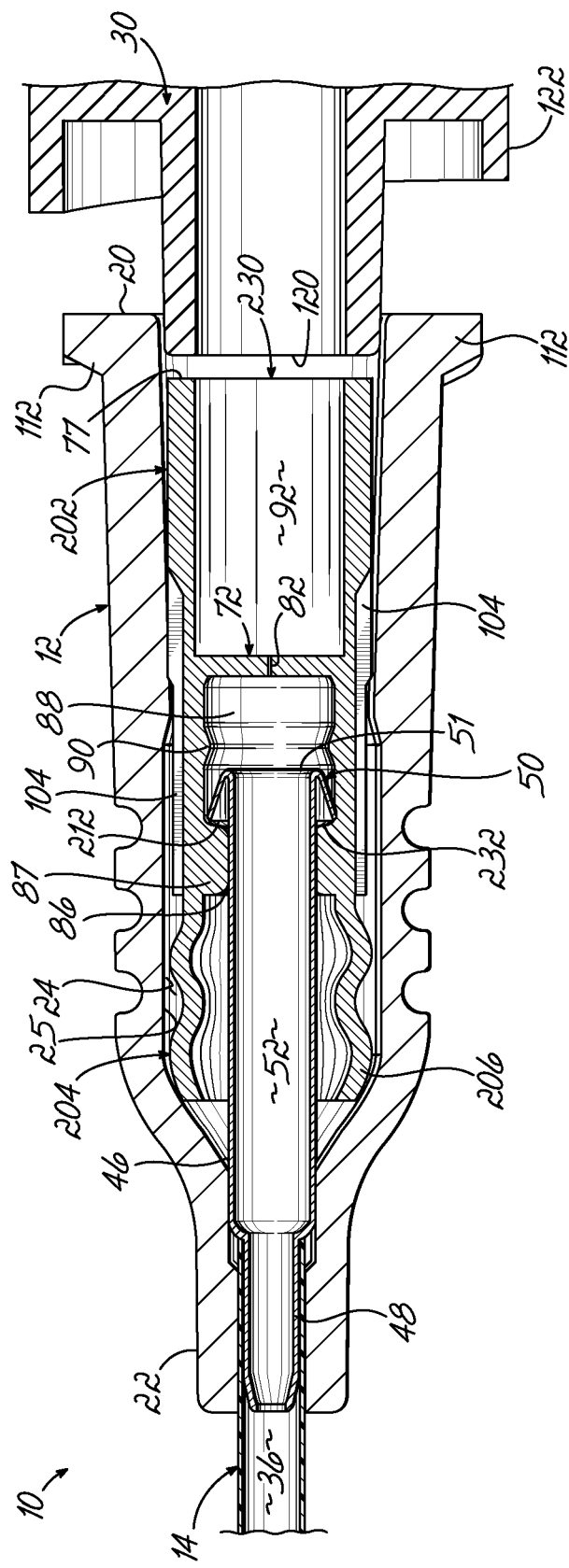
FIG. 17 is a partial, cross-sectional view of a catheter assembly similar to that shown in FIG. 14 having the biasing member partially compressed when the seal member is in the closed position.

In the embodiment shown in FIG. 14, when the seal member 200 is in the closed position, the biasing member 204 may not be subject to compression such that there is effectively no biasing force imposed on seal member 200 in the proximal direction due to biasing member 204. In an alternative embodiment, and as illustrated in FIG. 17 in which like reference numerals refer to like features in FIG. 14, a seal member 230 may be configured such that the biasing member 204 is partially compressed, therefore providing a biasing force in the proximal direction, when the seal member 230 is in the closed position. Providing this partial compression effectively increases the force on the seal member 230 during the period when the barb 50 is passing back through the membrane 72 as the seal member 230 is moving from the opened position toward the closed position.

In one embodiment, the partial compression of biasing member 204 may be achieved by essentially increasing the length of the biasing member 204 compared to that shown in FIG. 14. For example, in one embodiment, seal member 230 may be substantially identical to seal member 200, but for the tubular extension member 206 having an increased length. Alternatively, a seal member (not shown) may be substantially identical to seal member 220, but for the legs 224 having an increased length. To maintain the biasing member 204 in a partially compressed state when in the closed position, proximal movement of the seal member 230 is resisted by engagement between the barb 50 of actuator 16 and the actuator cavity 88. More particularly, the barb 50 is larger than the sealing outlet bore 86 of seal member 230 such that proximal movement of seal member 230 is arrested by the barb 50 bearing against a distal wall 232 of the actuator cavity 88. Though the biasing member 204 is partially compressed, those of ordinary skill in the art will understand that the operation of a catheter assembly having seal member 230 is similar to that described above and therefore a more detailed description of its operation will not be provided.

In the previous embodiments, the proximal free end 51 of actuator 16 includes a barb 50 that facilitates seating of the seal member on the actuator 16 and also prevents the seal member from being pulled proximally out of the catheter hub 12, such as for example, during withdrawal of the needle cannula 40 or the withdrawal of the nose 42 from the catheter hub 12. However, the barb 50 represents a resistance to free movement of the seal member from the opened position back to the closed position in the multi-use embodiments. In an alternative embodiment, the barb 50 may be omitted from the proximal free end 51 of the actuator so as to facilitate less restrictive movement of the seal member between the opened and closed positions. Accordingly, the seal member and the catheter hub cooperate in an alternative manner to retain the seal member therein during use.

In this regard and as illustrated in FIGS. 18 and 19, wherein like reference numerals refer to like features in the previous embodiments, a multi-use seal member 240 in accordance with an alternative embodiment includes a proximal portion 242 that is substantially similar to the seal member 18 shown in FIGS. 5-7 and described in detail above. Accordingly, the details of proximal portion 242 will not be further described. Additionally, seal member 240 includes a biasing member 204 extending distally from proximal portion 242 and integrally formed therewith so that seal member 240 forms a unitary member. In the illustrated embodiment, the biasing member 204 may include a proximal tubular extension portion 244 and a distal split tubular portion 246 having legs 248 defined by a pair of opposed slots 252 extending proximally from the distal end 210 of the biasing member 204. While in the illustrated embodiment, the slots 252 extend for only part of the length of the biasing member 204, in an alternative embodiment, the slots 252 may extend the full length of the biasing member 204 such that the biasing member 204 is similar to the legs 224 of seal member 220. In a further alternative embodiment, the slots 252 may be omitted such that the biasing member is similar to the tubular extension member 206 of seal member 200.

In these embodiments, the distal end 210 of the biasing member 204 includes a radially outwardly directed flange 254 on each of the legs 248 that in turn defines a proximally facing ledge or shoulder 256. As illustrated in FIG. 19, the flange 254 is configured to cooperate with an annular groove 258 formed in the inner wall 25 of the catheter hub 12. When the seal member 240 is properly positioned within the catheter hub 12, the flange 254 on each of the legs 248 is configured to be disposed within the annular groove or engage the annular groove 258 and thereby retain the seal member 240 within the catheter hub 12. For example, in one embodiment, the legs 248 may be biased radially outward (e.g., like a duckbill) so as to engage with the annular groove 258. The retention forces generated between the flanges 254 and the annular groove 258 are configured to be greater than the proximally directed forces on the seal member 240 during, for example, withdrawal of the needle cannula 40 from the catheter assembly 10 or the withdrawal of the nose 42 from the catheter hub 12. Accordingly, the seal member 240 remains in place within the catheter hub 12 during use.

Those of ordinary skill in the art will appreciate that the biasing member 204 as illustrated in FIGS. 18 and 19 will compress upon insertion of the male luer taper 30 in the catheter hub 12 similar to seal member 200 shown in FIG. 15. Those of ordinary skill in the art will further appreciate that the compression of biasing member 204 generates a return biasing force such that when the male luer taper 30 is removed from the catheter hub 12, the seal member 240 axially shifts from the opened position back toward the closed position to re-establish hemostasis. Without the barb 50 on actuator 16, it is expected that the force required to return the seal member 240 to the closed position is reduced. While seal member 240 is configured to be used when the barb 50 on actuator 16 is omitted, it should be recognized that the barb 50 may be used in combination with the flanges 254 and annular groove 258. It should be further recognized that in such an alternative embodiment, the biasing member 204 may be partially compressed similar to that shown in FIG. 17.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, in some applications, it may be desirable to enhance the securement of the seal member 18 within the catheter hub 12 such as with a retention mechanism which may be in the form of a radially inward annular rib (not shown) associated with the catheter hub inner wall 25 which mates with a corresponding annular groove (also not shown) in the seal member 18 in the closed position. However, when the male luer taper 30 is inserted into the catheter hub 12, as described above, this engagement is also overcome to allow the seal member 18 to be axially shifted to the opened position. Further, alternative assembly processes may be employed, one example of which utilizes a tool (not shown) having a shape similar to the nose 42 to insert the seal member 18 within the catheter hub 12. Once the tool positions the seal member 18 within the catheter hub 12, it may be removed therefrom. By way of further example, while slit 82 may be pre-cut into the membrane 72, the membrane 72 might not be pre-slit, but instead, may be pierced by the sharp tip 43 of the needle cannula 40 during assembly. When the needle cannula 40 is withdrawn from the membrane 72, the hole (not shown) caused by that piercing is capable of reclosing due to the resiliency of the membrane 72 so as to provide hemostasis. Even if the hole does not completely close, however, the hole would provide a significant restriction to blood flow through the membrane such that, for example, only a de minimus amount of blood would pass through the membrane 72 under normal use. It will be understood that the amount of force needed to actuate the seal member 18 may be slightly higher, and could also lead to permanent deformation or damage of the membrane 72 as the seal member 18 is moved to the opened position. Where the seal member is a one-time use seal as advantageously provided herein, such deformation or damage is not considered problematic. Furthermore, while the seal member 18 is described as a unitary member in the exemplary embodiment shown herein, in an alternative embodiment, the seal member may have a multi-piece construction. By way of example, the seal member may include a rigid retainer portion coupled to a resilient seal portion. The rigid retaining portion may be similar to the proximal portion 76 of the seal member 18 described above in that it may be generally cylindrical and include a nose receiving bore like bore 92 extending therethrough. The resilient seal portion may be similar to the membrane 72 and the distal portion 74 of the seal member 18 as described above. The resilient seal portion may be coupled to a distal end of the retainer portion and collectively have a shape similar to the seal member 18 above. The rigid retaining portion is configured to accommodate the stresses and forces imposed by the impact from the male luer taper 30, while the resilient seal portion is configured to provide the hemostasis function and accommodate passage of the barb 50 of the actuator 16 through the membrane 72 during actuation. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A catheter assembly having an actuator, the actuator comprising:
   a cylindrical shaft having a proximal free end, a distal end, and a first cross dimension;
   an eyelet portion extending from the distal end having an eyelet shaft of a second cross dimension;
   the proximal free end being configured to extend through a slit in a membrane; and
   the second cross dimension being sized less than the first cross dimension.

2. The catheter assembly of claim 1, wherein an end of the eyelet portion comprises a head that merges into an end of the cylindrical shaft to form an intersection.

3. The catheter assembly of claim 1, wherein the second cross dimension is sized closely to a diameter of a needle cannula inserted into the actuator from the proximal free end.

4. The catheter assembly of claim 1, wherein the eyelet portion is configured to secure to a catheter hub.

5. The catheter assembly of claim 1, further comprising a barb at the proximal free end of the cylindrical shaft, the barb including an enlarged flange folding back over a portion of the cylindrical shaft and diverging in a distal direction to define a frustoconical outer surface being radially outward of the cylindrical shaft and defining a third cross dimension, the third cross dimension being larger than the first cross dimension and the second cross dimension.

6. The catheter assembly of claim 5, wherein the barb comprises metal.

7. The catheter assembly of claim 1, wherein the actuator further comprises a surface feature.

8. The catheter assembly of claim 7, wherein the surface feature comprises at least one of an annular rib, a dimple, an annular groove, and an axial groove.

9. The catheter assembly of claim 1, wherein at least one of the cylindrical shaft and the eyelet portion comprises metal.

10. A catheter assembly comprising:
    a catheter hub having a proximal end and a distal end defining an interior cavity therebetween, with a catheter tube extending distally from the catheter hub distal end; and
    an actuator disposed within the catheter hub, comprising a cylindrical shaft having a proximal free end, a distal end, and a first cross dimension, an eyelet portion at the distal end having an eyelet shaft of a second cross dimension, the proximal free end being configured to extend through a slit in a membrane of a seal member provided within the catheter hub, the second cross dimension being sized less than the first cross dimension.

11. The catheter assembly of claim 10, wherein the second cross dimension is sized closely to a diameter of a needle cannula inserted into the actuator from the proximal free end.

12. The catheter assembly of claim 10, wherein the actuator is secured to the catheter hub by the eyelet portion.

13. The catheter assembly of claim 10, wherein the seal member includes an actuator cavity therein between the membrane and a sealing outlet bore, the actuator extending through the sealing outlet bore and out of the actuator cavity.

14. The catheter assembly of claim 13, wherein the seal member is axially slidable along the actuator to force the membrane over the free end of the actuator and open the membrane.

15. The catheter assembly of claim 13, wherein the membrane is slit to define slit flaps adapted to distend as the membrane is forced over the free end of the actuator.

16. The catheter assembly of claim 10, wherein the actuator further comprises a surface feature to enhance securement of the actuator to the catheter hub.

17. The catheter assembly of claim 16, wherein the surface feature comprises at least one of an annular rib, a dimple, an annular groove, and an axial groove.

* * * * *